US006911330B1

(12) United States Patent
Xia et al.

(10) Patent No.: US 6,911,330 B1
(45) Date of Patent: Jun. 28, 2005

(54) RECOMBINANT SECOISOLARICICIRESINOL DEHYDROGENSASE, AND METHODS OF USE

(75) Inventors: Zhi-Qiang Xia, Dedham, MA (US); Michael A. Costa, Pullman, WA (US); Laurence B. Davin, Pullman, WA (US); Norman G. Lewis, Pullman, WA (US)

(73) Assignee: Washington State University Research Foundation, Pullman, WA (US)

( * ) Notice: Subject to any disclaimer, the term of this patent is extended or adjusted under 35 U.S.C. 154(b) by 0 days.

(21) Appl. No.: 09/673,918

(22) PCT Filed: Apr. 23, 1999

(86) PCT No.: PCT/US99/08975

§ 371 (c)(1),
(2), (4) Date: Jan. 2, 2001

(87) PCT Pub. No.: WO99/55846

PCT Pub. Date: Nov. 4, 1999

Related U.S. Application Data

(60) Provisional application No. 60/082,977, filed on Apr. 24, 1998.

(51) Int. Cl.$^7$ .......................... C12N 9/04; C12N 15/00; C12N 1/20; C12Q 1/68; C07H 21/04
(52) U.S. Cl. ........................... 435/190; 435/6; 435/440; 435/252.3; 435/320.1; 536/252.3
(58) Field of Search ........................... 435/190, 6, 440, 435/252.3, 320.1, 325; 536/23.2

(56) References Cited

PUBLICATIONS

Herbers et al. Plant Mol. Biol. 29 (5), 1027–1038 (1995).*
Davin, L.B. et al., "Lignin and Lignan Biochemical Paathways in Plants: Unprecedented Discovery in Phenolic Coupling," *Anais de Academia Brasileira de Ciencias*, 67(3):363–378 (1995).
Umezawa et al., "Formation of Lignans (–)–Secoisolariciresinol and (–)–Matairesinol with Forsythia intermedia Cell–free Extracts," *J. Biol. Chem.*, 266(16):10210–10217 (1991).
Umezawa et al., *J. Chem. Soc., Chem Commun.*, 1990, 1405–1408.
Umezawa et al., *Biochem. Biophys. Res. Commun.*, 171(3):1008–1014 (1990).
Moenke, G., "Nicotiana tabacum mRNA for short chain alcohol dehydrogenase," *EMBL 'Online!*, (abstract) (1997).

Moenke, G., "Nicotiana tabacum scant gene," *EMBL 'Online!*, (abstract) (1998).
Iuchi, S., "Vigna unguiculata mRNA for CRPD12 protein," *EMBL 'Online!*, (abstract) (1997).
Davin, L.B. et al., "Purification of secoisolariciresinol dehydrogenase," *Plant Physiology*, (abstract) (1997).
Dinkova–Kostova, A. et al., "—Pinoresinol/(+)–lariciresinol reductase from Forsythia Intermedia: Protein Purification, cDNA cloning, heterologous expression and comparison to isoflavone reductase," Journal of Biological Chemistry, 271(46):29473–29482 (1996).
Davin, L.B. et al., "Lignin and Lignan Biochemical Paathways in Plants: Unprecedented Discovery in Phenolic Coupling,"*Anais da Academia Brasileira de Ciencias*, 67(3):363–378 (1995).
Umezawa et al., "Formation of Lignans (–)–Secoisolariciresinol and (–)–Matairesinol with Forsythia intermedia Cell–free Extracts," *J. Biol. Chem.*, 266(16):10210–10217 (1991).
Umezawa et al., *J. Chem. Soc. Chem. Commun.*, 1990, 1405–1408.
Umezawa et al., *Biochem. Biophys. Res. Commun.*, 17(3):1008–1014 (1990).

* cited by examiner

*Primary Examiner*—Ponnathapu Achutamurthy
*Assistant Examiner*—Yong D. Pak
(74) *Attorney, Agent, or Firm*—Christensen O'Connor Johnson Kindness PLLC

(57) ABSTRACT

A secoisolanciresinol dehydrogenase protein has been isolated from *Forsythia intermedia*, together with cDNAs encoding secoisolariciresinol dehydrogenase from this species. Accordingly, isolated DNA sequences are provided which code for the expression of secoisolariciresinol dehydrogenase. In other aspects, the present invention is directed to replicable recombinant cloning vehicles comprising a nucleic acid sequence which codes for a secoisolariciresinol dehydrogenase protein, or to a base sequence sufficiently complementary to at least a portion of a secoisolariciresinol dehydrogenase DNA or RNA to enable hybridization therewith. Thus, systems and methods are provided for the recombinant expression of secoisolariciresinol dehydrogenases that may be used to facilitate the production, isolation and purification of significant quantities of recombinant secoisolariciresinol dehydrogenase for subsequent use, to obtain expression or enhanced expression of secoisolariciresinol dehydrogenase in plants in order to enhance, or otherwise alter, lignan biosynthesis, or may be otherwise employed for the regulation or expression of secoisolariciresinol dehydrogenase.

6 Claims, 2 Drawing Sheets

SEQUENCE LISTING

```
<160> NUMBER OF SEQ ID NOS: 25

<210> SEQ ID NO 1
<211> LENGTH: 819
<212> TYPE: DNA
<213> ORGANISM: Forsythia x intermedia
<220> FEATURE:
<221> NAME/KEY: CDS
<222> LOCATION: (1)..(819)

<400> SEQUENCE: 1 atg cag ctt cga act gca ttc gca aga agg cta gaa gga aaa gtt gcc        48
Met Gln Leu Arg Thr Ala Phe Ala Arg Arg Leu Glu Gly Lys Val Ala
 1               5                  10                  15 ctt ata aca gga gga gcc agt gga att gga gaa acc aca gca aaa ctc        96
Leu Ile Thr Gly Gly Ala Ser Gly Ile Gly Glu Thr Thr Ala Lys Leu
            20                  25                  30 ttc tcc caa cat gga gcc aaa gtt gcc att gct gat gtc caa gat gaa       144
Phe Ser Gln His Gly Ala Lys Val Ala Ile Ala Asp Val Gln Asp Glu
        35                  40                  45 tta ggt cac tca gtt gtc gag gcc att ggc act tcc aat tcc acc tac       192
Leu Gly His Ser Val Val Glu Ala Ile Gly Thr Ser Asn Ser Thr Tyr
    50                  55                  60 atc cac tgt gat gtt act aat gaa gac ggt gtt aaa aat gcc gtg gac       240
Ile His Cys Asp Val Thr Asn Glu Asp Gly Val Lys Asn Ala Val Asp
65                  70                  75                  80 aac aca gtt tca acc tat gga aaa ctg gac att atg ttc agc aat gca       288
Asn Thr Val Ser Thr Tyr Gly Lys Leu Asp Ile Met Phe Ser Asn Ala
                85                  90                  95 gga att tct gat ccc aac agg ccc cgc atc ata gac aac gaa aaa gca       336
Gly Ile Ser Asp Pro Asn Arg Pro Arg Ile Ile Asp Asn Glu Lys Ala
            100                 105                 110 gac ttt gaa cgc gtt ctc agt gta aat gta acc gga gtt ttc cta tgc       384
Asp Phe Glu Arg Val Leu Ser Val Asn Val Thr Gly Val Phe Leu Cys
        115                 120                 125
```

```
atg aag cac gca gca cgt gtt atg att cca gca cgc agt ggc aac ata       432
Met Lys His Ala Ala Arg Val Met Ile Pro Ala Arg Ser Gly Asn Ile
    130                 135                 140 att tcc act gct agt tta agc tca act atg ggt ggt ggt tct tca cat       480
Ile Ser Thr Ala Ser Leu Ser Ser Thr Met Gly Gly Gly Ser Ser His
145                 150                 155                 160 gcc tat tgt ggt tca aag cat gct gtg tta gcc ctt act agg aat ctg       528
Ala Tyr Cys Gly Ser Lys His Ala Val Leu Ala Leu Thr Arg Asn Leu
                165                 170                 175 gca gtc gag ctc gga caa ttt ggc att agg gtt aat tgt ttg tct cct       576
Ala Val Glu Leu Gly Gln Phe Gly Ile Arg Val Asn Cys Leu Ser Pro
            180                 185                 190 ttc ggg ctt cct acg gct tta ggc aag aaa ttt tca ggg att aaa aat       624
Phe Gly Leu Pro Thr Ala Leu Gly Lys Lys Phe Ser Gly Ile Lys Asn
        195                 200                 205 gaa gaa gaa ttt gag aat gta ata aac ttt gcg gga aat ttg aaa ggt       672
Glu Glu Glu Phe Glu Asn Val Ile Asn Phe Ala Gly Asn Leu Lys Gly
    210                 215                 220 cca aaa ttt aat gtt gag gat gtt gcc aat gca gct ctt tat ctg gct       720
Pro Lys Phe Asn Val Glu Asp Val Ala Asn Ala Ala Leu Tyr Leu Ala
225                 230                 235                 240 agt gat gag gca aaa tac gtg agt gga cac aat ctg ttc att gat gga       768
Ser Asp Glu Ala Lys Tyr Val Ser Gly His Asn Leu Phe Ile Asp Gly
                245                 250                 255 ggg ttc agc gtc tgc aat tct gta atc aaa gtg ttc caa tat cca gat       816
Gly Phe Ser Val Cys Asn Ser Val Ile Lys Val Phe Gln Tyr Pro Asp
            260                 265                 270 tct                                                                    819
Ser

<210> SEQ ID NO 2
<211> LENGTH: 273
<212> TYPE: PRT
<213> ORGANISM: Forsythia x intermedia

<400> SEQUENCE: 2

Met Gln Leu Arg Thr Ala Phe Ala Arg Arg Leu Glu Gly Lys Val Ala
1               5                   10                  15

Leu Ile Thr Gly Gly Ala Ser Gly Ile Gly Glu Thr Thr Ala Lys Leu
            20                  25                  30

Phe Ser Gln His Gly Ala Lys Val Ala Ile Ala Asp Val Gln Asp Glu
        35                  40                  45

Leu Gly His Ser Val Val Glu Ala Ile Gly Thr Ser Asn Ser Thr Tyr
    50                  55                  60

Ile His Cys Asp Val Thr Asn Glu Asp Gly Val Lys Asn Ala Val Asp
65                  70                  75                  80

Asn Thr Val Ser Thr Tyr Gly Lys Leu Asp Ile Met Phe Ser Asn Ala
                85                  90                  95

Gly Ile Ser Asp Pro Asn Arg Pro Arg Ile Ile Asp Asn Glu Lys Ala
            100                 105                 110

Asp Phe Glu Arg Val Leu Ser Val Asn Val Thr Gly Val Phe Leu Cys
        115                 120                 125

Met Lys His Ala Ala Arg Val Met Ile Pro Ala Arg Ser Gly Asn Ile
    130                 135                 140

Ile Ser Thr Ala Ser Leu Ser Ser Thr Met Gly Gly Gly Ser Ser His
145                 150                 155                 160

Ala Tyr Cys Gly Ser Lys His Ala Val Leu Ala Leu Thr Arg Asn Leu
                165                 170                 175
```

```
Ala Val Glu Leu Gly Gln Phe Gly Ile Arg Val Asn Cys Leu Ser Pro
            180                 185                 190

Phe Gly Leu Pro Thr Ala Leu Gly Lys Lys Phe Ser Gly Ile Lys Asn
            195                 200                 205

Glu Glu Glu Phe Glu Asn Val Ile Asn Phe Ala Gly Asn Leu Lys Gly
        210                 215                 220

Pro Lys Phe Asn Val Glu Asp Val Ala Asn Ala Leu Tyr Leu Ala
225                 230                 235                 240

Ser Asp Glu Ala Lys Tyr Val Ser Gly His Asn Leu Phe Ile Asp Gly
                245                 250                 255

Gly Phe Ser Val Cys Asn Ser Val Ile Lys Val Phe Gln Tyr Pro Asp
            260                 265                 270

Ser

<210> SEQ ID NO 3
<211> LENGTH: 831
<212> TYPE: DNA
<213> ORGANISM: Forsythia x intermedia
<220> FEATURE:
<221> NAME/KEY: CDS
<222> LOCATION: (1)..(831)

<400> SEQUENCE: 3 atg gca gcc act tca cag gtt cta act gca atc gca aga agg cta gaa       48
Met Ala Ala Thr Ser Gln Val Leu Thr Ala Ile Ala Arg Arg Leu Glu
 1               5                  10                  15 gga aaa gtt gcc ctt ata aca gga gga gcc agt gga att gga gaa acc       96
Gly Lys Val Ala Leu Ile Thr Gly Gly Ala Ser Gly Ile Gly Glu Thr
            20                  25                  30 aca gca aaa ctc ttc tcc caa cat gga gcc aaa gtt gcc att gct gat      144
Thr Ala Lys Leu Phe Ser Gln His Gly Ala Lys Val Ala Ile Ala Asp
        35                  40                  45 gtc caa gat gaa tta ggt cac tca gtt gtc gag gcc att ggc act tcc      192
Val Gln Asp Glu Leu Gly His Ser Val Val Glu Ala Ile Gly Thr Ser
 50                  55                  60 aat tcc acc tac atc cac tgt gat gtt act aat gaa gac ggt gtt aaa      240
Asn Ser Thr Tyr Ile His Cys Asp Val Thr Asn Glu Asp Gly Val Lys
 65                  70                  75                  80 aat gcc gtg gac aac aca gtt tca acc tat gga aaa ctg gac att atg      288
Asn Ala Val Asp Asn Thr Val Ser Thr Tyr Gly Lys Leu Asp Ile Met
                85                  90                  95 ttc agc aat gca gga att tct gat ccc aac agg ccc cgc atc ata gac      336
Phe Ser Asn Ala Gly Ile Ser Asp Pro Asn Arg Pro Arg Ile Ile Asp
            100                 105                 110 aac gaa aaa gca gac ttt gaa cgc gtt ttc agt gta aat gta acc gga      384
Asn Glu Lys Ala Asp Phe Glu Arg Val Phe Ser Val Asn Val Thr Gly
        115                 120                 125 gtt ttc cta tgc atg aag cac gca gca cgt gtt atg att cca gca cgc      432
Val Phe Leu Cys Met Lys His Ala Ala Arg Val Met Ile Pro Ala Arg
130                 135                 140 agt ggc aac ata att tcc act gct agt tta agc tca act atg ggt ggt      480
Ser Gly Asn Ile Ile Ser Thr Ala Ser Leu Ser Ser Thr Met Gly Gly
145                 150                 155                 160 ggt tct tca cat gcc tat tgt ggt tca aag cat gct gtg tta ggc ctt      528
Gly Ser Ser His Ala Tyr Cys Gly Ser Lys His Ala Val Leu Gly Leu
                165                 170                 175 act agg aat ctg gca gtc gag ctc gga caa ttt ggc att agg gtt aat      576
Thr Arg Asn Leu Ala Val Glu Leu Gly Gln Phe Gly Ile Arg Val Asn
            180                 185                 190
```

-continued

```
tgt ttg tct cct ttc ggg ctt cct acg gct tta ggc aag aaa ttt tca      624
Cys Leu Ser Pro Phe Gly Leu Pro Thr Ala Leu Gly Lys Lys Phe Ser
        195                 200                 205 ggg att aaa aat gaa gaa gaa ttt gag aat gta ata aac ttt gcg gga      672
Gly Ile Lys Asn Glu Glu Glu Phe Glu Asn Val Ile Asn Phe Ala Gly
210                 215                 220 aat ctg aaa ggt cca aaa ttt aat gtt gag gat gtt gcc aat gca gct      720
Asn Leu Lys Gly Pro Lys Phe Asn Val Glu Asp Val Ala Asn Ala Ala
225                 230                 235                 240 ctt tat ctg gct agt gat gag gca aaa tac gtg agt gga cac aat ctg      768
Leu Tyr Leu Ala Ser Asp Glu Ala Lys Tyr Val Ser Gly His Asn Leu
                245                 250                 255 ttc att gat gga ggg ttc agc gtc tgc aat tct gta atc aaa gtg ttc      816
Phe Ile Asp Gly Gly Phe Ser Val Cys Asn Ser Val Ile Lys Val Phe
            260                 265                 270 caa tat cca gat tct                                                   831
Gln Tyr Pro Asp Ser
        275
```

<210> SEQ ID NO 4
<211> LENGTH: 277
<212> TYPE: PRT
<213> ORGANISM: Forsythia x intermedia

<400> SEQUENCE: 4

```
Met Ala Ala Thr Ser Gln Val Leu Thr Ala Ile Ala Arg Arg Leu Glu
 1               5                  10                  15

Gly Lys Val Ala Leu Ile Thr Gly Gly Ala Ser Gly Ile Gly Glu Thr
            20                  25                  30

Thr Ala Lys Leu Phe Ser Gln His Gly Ala Lys Val Ala Ile Ala Asp
        35                  40                  45

Val Gln Asp Glu Leu Gly His Ser Val Val Glu Ala Ile Gly Thr Ser
    50                  55                  60

Asn Ser Thr Tyr Ile His Cys Asp Val Thr Asn Glu Asp Gly Val Lys
65                  70                  75                  80

Asn Ala Val Asp Asn Thr Val Ser Thr Tyr Gly Lys Leu Asp Ile Met
                85                  90                  95

Phe Ser Asn Ala Gly Ile Ser Asp Pro Asn Arg Pro Arg Ile Ile Asp
            100                 105                 110

Asn Glu Lys Ala Asp Phe Glu Arg Val Phe Ser Val Asn Val Thr Gly
        115                 120                 125

Val Phe Leu Cys Met Lys His Ala Ala Arg Val Met Ile Pro Ala Arg
    130                 135                 140

Ser Gly Asn Ile Ile Ser Thr Ala Ser Leu Ser Ser Thr Met Gly Gly
145                 150                 155                 160

Gly Ser Ser His Ala Tyr Cys Gly Ser Lys His Ala Val Leu Gly Leu
                165                 170                 175

Thr Arg Asn Leu Ala Val Glu Leu Gly Gln Phe Gly Ile Arg Val Asn
            180                 185                 190

Cys Leu Ser Pro Phe Gly Leu Pro Thr Ala Leu Gly Lys Lys Phe Ser
        195                 200                 205

Gly Ile Lys Asn Glu Glu Glu Phe Glu Asn Val Ile Asn Phe Ala Gly
    210                 215                 220

Asn Leu Lys Gly Pro Lys Phe Asn Val Glu Asp Val Ala Asn Ala Ala
225                 230                 235                 240

Leu Tyr Leu Ala Ser Asp Glu Ala Lys Tyr Val Ser Gly His Asn Leu
                245                 250                 255
```

```
        Phe Ile Asp Gly Gly Phe Ser Val Cys Asn Ser Val Ile Lys Val Phe
                    260                 265                 270

Gln Tyr Pro Asp Ser
                275

<210> SEQ ID NO 5
<211> LENGTH: 819
<212> TYPE: DNA
<213> ORGANISM: Forsythia x intermedia
<220> FEATURE:
<221> NAME/KEY: CDS
<222> LOCATION: (1)..(819)
<220> FEATURE:
<221> NAME/KEY: misc_feature
<222> LOCATION: (1)..(819)
<223> OTHER INFORMATION: cDNA molecule encoding secoisolariciresinol
      dehydrogenase wherein Xaa = any amino acid

<400> SEQUENCE: 5 atg cag ctt cga act gca atc gca aga agg cta gaa gga aaa gtt gcc      48
Met Gln Leu Arg Thr Ala Ile Ala Arg Arg Leu Glu Gly Lys Val Ala
 1               5                  10                  15 ctt ata aca gga gga gcc agt gga gtt gga gaa gtc aca gca aaa ctc      96
Leu Ile Thr Gly Gly Ala Ser Gly Val Gly Glu Val Thr Ala Lys Leu
            20                  25                  30 ttc tcc caa cat gga gcc aaa gtt gcc att gct gat gtc caa gat gaa     144
Phe Ser Gln His Gly Ala Lys Val Ala Ile Ala Asp Val Gln Asp Glu
        35                  40                  45 tta ggt cac tca gtt gtc gag gcc att ggc cct tcc aat tcc acc tac     192
Leu Gly His Ser Val Val Glu Ala Ile Gly Pro Ser Asn Ser Thr Tyr
    50                  55                  60 atc cac tgc gat gtt act aat gaa gac ggt gtt aaa aat gcc gtg gac     240
Ile His Cys Asp Val Thr Asn Glu Asp Gly Val Lys Asn Ala Val Asp
65                  70                  75                  80 aac aca gtt tca acc tat gga aaa ctg gac att atg ttc aac aat gca     288
Asn Thr Val Ser Thr Tyr Gly Lys Leu Asp Ile Met Phe Asn Asn Ala
                85                  90                  95 gga att tct gat ccc tac aag ccc cgg gtc ata gac aac gaa aaa gca     336
Gly Ile Ser Asp Pro Tyr Lys Pro Arg Val Ile Asp Asn Glu Lys Ala
            100                 105                 110 gac ttt gaa cgc gtt ctc agt gtn aat gtn acc gga gtt ttc cta ttt     384
Asp Phe Glu Arg Val Leu Ser Xaa Asn Xaa Thr Gly Val Phe Leu Phe
        115                 120                 125 atg aag cac gca gca cgc att atg gtt cca gca cga aat ggc tgc ata     432
Met Lys His Ala Ala Arg Ile Met Val Pro Ala Arg Asn Gly Cys Ile
    130                 135                 140 att tcc act gct agt tta agc tca act atg ggt ggt ggt tct tca cat     480
Ile Ser Thr Ala Ser Leu Ser Ser Thr Met Gly Gly Gly Ser Ser His
145                 150                 155                 160 gct tat tgt ggt gca aaa cat gct gta tta ggc ctt act agg aat ctg     528
Ala Tyr Cys Gly Ala Lys His Ala Val Leu Gly Leu Thr Arg Asn Leu
                165                 170                 175 gca gtc gag ctc gga caa ttt ggc att agg gtt aat tgt ttg tct cct     576
Ala Val Glu Leu Gly Gln Phe Gly Ile Arg Val Asn Cys Leu Ser Pro
            180                 185                 190 ttc ggg ctt cct acg cct cta gcc aag aaa ttt tca ggg att gaa aat     624
Phe Gly Leu Pro Thr Pro Leu Ala Lys Lys Phe Ser Gly Ile Glu Asn
        195                 200                 205 gat gta gac ttt gcg aat gca ata gaa cat gcg gga aat ctg aaa ggt     672
Asp Val Asp Phe Ala Asn Ala Ile Glu His Ala Gly Asn Leu Lys Gly
    210                 215                 220
```

```
aca aaa ttg agg att gag gat gtt gcc aat gca gct ctt ttt ctg gct    720
Thr Lys Leu Arg Ile Glu Asp Val Ala Asn Ala Ala Leu Phe Leu Ala
225             230                 235                 240 agt gat gag gca caa tat gtg agt gga caa aat ctg ttc atc gat gga    768
Ser Asp Glu Ala Gln Tyr Val Ser Gly Gln Asn Leu Phe Ile Asp Gly
            245                 250                 255 ggg ttc agc gtc tgc aat tct gca atc aaa atg ttc caa tat cca gac    816
Gly Phe Ser Val Cys Asn Ser Ala Ile Lys Met Phe Gln Tyr Pro Asp
        260                 265                 270 tct                                                                819
Ser
```

<210> SEQ ID NO 6
<211> LENGTH: 273
<212> TYPE: PRT
<213> ORGANISM: Forsythia x intermedia
<220> FEATURE:
<221> NAME/KEY: misc_feature
<222> LOCATION: (1)..(273)
<223> OTHER INFORMATION: Secoisolariciresinol dehydrogenase wherein
      Xaa = any amino acid

<400> SEQUENCE: 6

```
Met Gln Leu Arg Thr Ala Ile Ala Arg Arg Leu Glu Gly Lys Val Ala
  1               5                  10                  15

Leu Ile Thr Gly Gly Ala Ser Gly Val Gly Glu Val Thr Ala Lys Leu
             20                  25                  30

Phe Ser Gln His Gly Ala Lys Val Ala Ile Ala Asp Val Gln Asp Glu
         35                  40                  45

Leu Gly His Ser Val Val Glu Ala Ile Gly Pro Ser Asn Ser Thr Tyr
     50                  55                  60

Ile His Cys Asp Val Thr Asn Glu Asp Gly Val Lys Asn Ala Val Asp
 65                  70                  75                  80

Asn Thr Val Ser Thr Tyr Gly Lys Leu Asp Ile Met Phe Asn Asn Ala
                 85                  90                  95

Gly Ile Ser Asp Pro Tyr Lys Pro Arg Val Ile Asp Asn Glu Lys Ala
            100                 105                 110

Asp Phe Glu Arg Val Leu Ser Xaa Asn Xaa Thr Gly Val Phe Leu Phe
        115                 120                 125

Met Lys His Ala Ala Arg Ile Met Val Pro Ala Arg Asn Gly Cys Ile
    130                 135                 140

Ile Ser Thr Ala Ser Leu Ser Ser Thr Met Gly Gly Gly Ser Ser His
145                 150                 155                 160

Ala Tyr Cys Gly Ala Lys His Ala Val Leu Gly Leu Thr Arg Asn Leu
                165                 170                 175

Ala Val Glu Leu Gly Gln Phe Gly Ile Arg Val Asn Cys Leu Ser Pro
            180                 185                 190

Phe Gly Leu Pro Thr Pro Leu Ala Lys Lys Phe Ser Gly Ile Glu Asn
        195                 200                 205

Asp Val Asp Phe Ala Asn Ala Ile Glu His Ala Gly Asn Leu Lys Gly
    210                 215                 220

Thr Lys Leu Arg Ile Glu Asp Val Ala Asn Ala Ala Leu Phe Leu Ala
225                 230                 235                 240

Ser Asp Glu Ala Gln Tyr Val Ser Gly Gln Asn Leu Phe Ile Asp Gly
                245                 250                 255
```

```
Gly Phe Ser Val Cys Asn Ser Ala Ile Lys Met Phe Gln Tyr Pro Asp
            260                 265                 270
Ser
```

```
<210> SEQ ID NO 7
<211> LENGTH: 831
<212> TYPE: DNA
<213> ORGANISM: Forsythia x intermedia
<220> FEATURE:
<221> NAME/KEY: CDS
<222> LOCATION: (1)..(831)

<400> SEQUENCE: 7
```

| | | | | | | | | | | | | | | | | |
|---|---|---|---|---|---|---|---|---|---|---|---|---|---|---|---|---|
| atg | gcc | agt | act | tca | cag | gtt | cta | act | gca | atc | aca | aga | agg | cta | gaa | 48 |
| Met | Ala | Ser | Thr | Ser | Gln | Val | Leu | Thr | Ala | Ile | Thr | Arg | Arg | Leu | Glu | |
| 1 | | | | 5 | | | | | 10 | | | | | 15 | | |
| gga | aaa | gtt | gcc | ctt | ata | aca | gga | gga | gcc | agt | gga | att | gga | gaa | ttc | 96 |
| Gly | Lys | Val | Ala | Leu | Ile | Thr | Gly | Gly | Ala | Ser | Gly | Ile | Gly | Glu | Phe | |
| | | | 20 | | | | | 25 | | | | | 30 | | | |
| aca | gca | aaa | ctc | ttc | tcc | caa | cat | gga | gcc | aaa | gtt | gcc | att | gct | gat | 144 |
| Thr | Ala | Lys | Leu | Phe | Ser | Gln | His | Gly | Ala | Lys | Val | Ala | Ile | Ala | Asp | |
| | | 35 | | | | | 40 | | | | | 45 | | | | |
| gtc | caa | gat | gaa | tta | ggt | cac | tca | gtt | gtc | gag | gcc | atc | ggc | act | tcc | 192 |
| Val | Gln | Asp | Glu | Leu | Gly | His | Ser | Val | Val | Glu | Ala | Ile | Gly | Thr | Ser | |
| | 50 | | | | | 55 | | | | | 60 | | | | | |
| aat | tcc | atc | tac | atc | cac | tgc | gat | gtt | acc | aat | gaa | gac | gat | gtt | aaa | 240 |
| Asn | Ser | Ile | Tyr | Ile | His | Cys | Asp | Val | Thr | Asn | Glu | Asp | Asp | Val | Lys | |
| 65 | | | | | 70 | | | | | 75 | | | | | 80 | |
| aat | gcc | gtg | gac | aac | aca | gtt | tca | acc | tat | gga | aaa | ctg | gac | att | atg | 288 |
| Asn | Ala | Val | Asp | Asn | Thr | Val | Ser | Thr | Tyr | Gly | Lys | Leu | Asp | Ile | Met | |
| | | | | 85 | | | | | 90 | | | | | 95 | | |
| ttc | aac | aat | gca | gga | att | gct | gac | ccc | aac | aag | ccc | cgc | atc | gta | gac | 336 |
| Phe | Asn | Asn | Ala | Gly | Ile | Ala | Asp | Pro | Asn | Lys | Pro | Arg | Ile | Val | Asp | |
| | | | 100 | | | | | 105 | | | | | 110 | | | |
| aac | gaa | aaa | gca | gac | ttt | gaa | cgc | gtt | ctc | agc | gta | aat | gta | acc | ggt | 384 |
| Asn | Glu | Lys | Ala | Asp | Phe | Glu | Arg | Val | Leu | Ser | Val | Asn | Val | Thr | Gly | |
| | | 115 | | | | | 120 | | | | | 125 | | | | |
| gtt | ttc | cta | tgc | atg | aag | cac | gca | gca | cgc | gtt | atg | gtg | cca | gca | cgc | 432 |
| Val | Phe | Leu | Cys | Met | Lys | His | Ala | Ala | Arg | Val | Met | Val | Pro | Ala | Arg | |
| | 130 | | | | | 135 | | | | | 140 | | | | | |
| agc | ggc | agc | ata | att | tcc | act | gct | agc | gta | agc | tca | aca | att | ggt | ggt | 480 |
| Ser | Gly | Ser | Ile | Ile | Ser | Thr | Ala | Ser | Val | Ser | Ser | Thr | Ile | Gly | Gly | |
| 145 | | | | | 150 | | | | | 155 | | | | | 160 | |
| gct | gct | tca | cat | gct | tat | tgt | tgt | tca | aag | cat | gct | gtg | tta | ggc | ctt | 528 |
| Ala | Ala | Ser | His | Ala | Tyr | Cys | Cys | Ser | Lys | His | Ala | Val | Leu | Gly | Leu | |
| | | | | 165 | | | | | 170 | | | | | 175 | | |
| act | agg | aat | ctg | gca | gtc | gag | ctc | gga | caa | ttt | ggc | att | agg | gtt | aat | 576 |
| Thr | Arg | Asn | Leu | Ala | Val | Glu | Leu | Gly | Gln | Phe | Gly | Ile | Arg | Val | Asn | |
| | | | 180 | | | | | 185 | | | | | 190 | | | |
| tgt | ttg | gct | cct | tac | gcg | ctt | gct | acg | cct | tta | gcc | aag | aaa | ttt | gta | 624 |
| Cys | Leu | Ala | Pro | Tyr | Ala | Leu | Ala | Thr | Pro | Leu | Ala | Lys | Lys | Phe | Val | |
| | | 195 | | | | | 200 | | | | | 205 | | | | |
| ggg | ctt | gaa | aat | gac | gaa | gat | ttg | gag | aat | gca | atg | agc | ctt | atg | gga | 672 |
| Gly | Leu | Glu | Asn | Asp | Glu | Asp | Leu | Glu | Asn | Ala | Met | Ser | Leu | Met | Gly | |
| | 210 | | | | | 215 | | | | | 220 | | | | | |
| aat | ctg | aaa | ggt | aca | aat | ttg | aag | gct | gag | gac | gtc | gcc | aat | gca | gct | 720 |
| Asn | Leu | Lys | Gly | Thr | Asn | Leu | Lys | Ala | Glu | Asp | Val | Ala | Asn | Ala | Ala | |
| 225 | | | | | 230 | | | | | 235 | | | | | 240 | |
| ctt | tat | ctg | gca | agt | gat | gag | gca | aaa | tat | gtg | agt | gga | cac | aat | ctg | 768 |
| Leu | Tyr | Leu | Ala | Ser | Asp | Glu | Ala | Lys | Tyr | Val | Ser | Gly | His | Asn | Leu | |
| | | | | 245 | | | | | 250 | | | | | 255 | | |

-continued

```
ttc att gat gga ggg ttc agc gtc tac aat tct gca atc aaa atg ttc         816
Phe Ile Asp Gly Gly Phe Ser Val Tyr Asn Ser Ala Ile Lys Met Phe
        260                 265                 270 caa tat cca gac act                                                      831
Gln Tyr Pro Asp Thr
        275
```

<210> SEQ ID NO 8
<211> LENGTH: 277
<212> TYPE: PRT
<213> ORGANISM: Forsythia x intermedia

<400> SEQUENCE: 8

```
Met Ala Ser Thr Ser Gln Val Leu Thr Ala Ile Thr Arg Arg Leu Glu
  1               5                  10                  15

Gly Lys Val Ala Leu Ile Thr Gly Gly Ala Ser Gly Ile Gly Glu Phe
             20                  25                  30

Thr Ala Lys Leu Phe Ser Gln His Gly Ala Lys Val Ala Ile Ala Asp
         35                  40                  45

Val Gln Asp Glu Leu Gly His Ser Val Val Glu Ala Ile Gly Thr Ser
     50                  55                  60

Asn Ser Ile Tyr Ile His Cys Asp Val Thr Asn Glu Asp Asp Val Lys
 65                  70                  75                  80

Asn Ala Val Asp Asn Thr Val Ser Thr Tyr Gly Lys Leu Asp Ile Met
                 85                  90                  95

Phe Asn Asn Ala Gly Ile Ala Asp Pro Asn Lys Pro Arg Ile Val Asp
            100                 105                 110

Asn Glu Lys Ala Asp Phe Glu Arg Val Leu Ser Val Asn Val Thr Gly
        115                 120                 125

Val Phe Leu Cys Met Lys His Ala Ala Arg Val Met Val Pro Ala Arg
    130                 135                 140

Ser Gly Ser Ile Ile Ser Thr Ala Ser Val Ser Ser Thr Ile Gly Gly
145                 150                 155                 160

Ala Ala Ser His Ala Tyr Cys Cys Ser Lys His Ala Val Leu Gly Leu
                165                 170                 175

Thr Arg Asn Leu Ala Val Glu Leu Gly Gln Phe Gly Ile Arg Val Asn
            180                 185                 190

Cys Leu Ala Pro Tyr Ala Leu Ala Thr Pro Leu Ala Lys Lys Phe Val
        195                 200                 205

Gly Leu Glu Asn Asp Glu Asp Leu Glu Asn Ala Met Ser Leu Met Gly
    210                 215                 220

Asn Leu Lys Gly Thr Asn Leu Lys Ala Glu Asp Val Ala Asn Ala Ala
225                 230                 235                 240

Leu Tyr Leu Ala Ser Asp Glu Ala Lys Tyr Val Ser Gly His Asn Leu
                245                 250                 255

Phe Ile Asp Gly Gly Phe Ser Val Tyr Asn Ser Ala Ile Lys Met Phe
            260                 265                 270

Gln Tyr Pro Asp Thr
        275
```

<210> SEQ ID NO 9
<211> LENGTH: 828
<212> TYPE: DNA
<213> ORGANISM: Forsythia x intermedia
<220> FEATURE:
<221> NAME/KEY: CDS
<222> LOCATION: (1)..(828)

-continued

```
<400> SEQUENCE: 9 atg gcc act tca cag ctt cga act gca ttc gca aga agg cta gaa gga    48
Met Ala Thr Ser Gln Leu Arg Thr Ala Phe Ala Arg Arg Leu Glu Gly
 1               5                  10                  15 aaa gtt gcc ctt ata aca gga gga gcc agt gga gtt gga gaa gtc aca    96
Lys Val Ala Leu Ile Thr Gly Gly Ala Ser Gly Val Gly Glu Val Thr
             20                  25                  30 gca aaa ctc ttc tcc caa cat gga gcc aaa gtt gcc att gct gat gtc   144
Ala Lys Leu Phe Ser Gln His Gly Ala Lys Val Ala Ile Ala Asp Val
         35                  40                  45 caa gat gaa tta ggt cac tca gtt gtc gag gcc att ggc ctt tcc aat   192
Gln Asp Glu Leu Gly His Ser Val Val Glu Ala Ile Gly Leu Ser Asn
     50                  55                  60 tcc acc tac atc cac tgc gat gtt act aat gaa gac ggt gtt aaa aat   240
Ser Thr Tyr Ile His Cys Asp Val Thr Asn Glu Asp Gly Val Lys Asn
 65                  70                  75                  80 gcc gtg gac aac aca gtt tca acc tat gga aaa ctg gac att atg ttc   288
Ala Val Asp Asn Thr Val Ser Thr Tyr Gly Lys Leu Asp Ile Met Phe
                 85                  90                  95 aac aat gca gga att tct gat ccc tac aag ccc cgg gtc ata gac aac   336
Asn Asn Ala Gly Ile Ser Asp Pro Tyr Lys Pro Arg Val Ile Asp Asn
            100                 105                 110 gaa aaa gca gac ttt gaa cgc gtt ctc agt gtt aat gta acc gga gtt   384
Glu Lys Ala Asp Phe Glu Arg Val Leu Ser Val Asn Val Thr Gly Val
        115                 120                 125 ttc cta ttt atg aag cac gca gca cgc att atg gtt cca gca cga agt   432
Phe Leu Phe Met Lys His Ala Ala Arg Ile Met Val Pro Ala Arg Ser
    130                 135                 140 ggc tgc ata att tcc act gct agt tta agc tca act atg ggt ggt ggt   480
Gly Cys Ile Ile Ser Thr Ala Ser Leu Ser Ser Thr Met Gly Gly Gly
145                 150                 155                 160 tct tca cat gct tat tgt ggt tca aag cat gct gta tta ggc ctt act   528
Ser Ser His Ala Tyr Cys Gly Ser Lys His Ala Val Leu Gly Leu Thr
                165                 170                 175 agg aat ctg gca gtc gag ctc gga caa ttt ggc att agg gtt aat tgt   576
Arg Asn Leu Ala Val Glu Leu Gly Gln Phe Gly Ile Arg Val Asn Cys
            180                 185                 190 ttg tct cct ttc ggg ctt cct acg cct tta gcc aag aaa ttt aca ggg   624
Leu Ser Pro Phe Gly Leu Pro Thr Pro Leu Ala Lys Lys Phe Thr Gly
        195                 200                 205 att gaa aat gat gaa gac ttg gcg aat gga ata gaa cgt gcg gga aat   672
Ile Glu Asn Asp Glu Asp Leu Ala Asn Gly Ile Glu Arg Ala Gly Asn
    210                 215                 220 ctg aaa ggt aca aaa ttg agg att gag gat gtt gcc aat gca gct ctt   720
Leu Lys Gly Thr Lys Leu Arg Ile Glu Asp Val Ala Asn Ala Ala Leu
225                 230                 235                 240 ttt ctg gct agt gat gag gca caa tat gtg agt gga caa aat ctg ttc   768
Phe Leu Ala Ser Asp Glu Ala Gln Tyr Val Ser Gly Gln Asn Leu Phe
                245                 250                 255 atc gat gga ggg ttc agc gtc tgc aat tct gca atc aaa ttg ttc caa   816
Ile Asp Gly Gly Phe Ser Val Cys Asn Ser Ala Ile Lys Leu Phe Gln
            260                 265                 270 tat cca gac tct                                                   828
Tyr Pro Asp Ser
        275

<210> SEQ ID NO 10
<211> LENGTH: 276
<212> TYPE: PRT
<213> ORGANISM: Forsythia x intermedia
```

```
<400> SEQUENCE: 10

Met Ala Thr Ser Gln Leu Arg Thr Ala Phe Ala Arg Arg Leu Glu Gly
  1               5                  10                  15

Lys Val Ala Leu Ile Thr Gly Gly Ala Ser Gly Val Gly Glu Val Thr
             20                  25                  30

Ala Lys Leu Phe Ser Gln His Gly Ala Lys Val Ala Ile Ala Asp Val
         35                  40                  45

Gln Asp Glu Leu Gly His Ser Val Val Glu Ala Ile Gly Leu Ser Asn
     50                  55                  60

Ser Thr Tyr Ile His Cys Asp Val Thr Asn Glu Asp Gly Val Lys Asn
 65                  70                  75                  80

Ala Val Asp Asn Thr Val Ser Thr Tyr Gly Lys Leu Asp Ile Met Phe
             85                  90                  95

Asn Asn Ala Gly Ile Ser Asp Pro Tyr Lys Pro Arg Val Ile Asp Asn
            100                 105                 110

Glu Lys Ala Asp Phe Glu Arg Val Leu Ser Val Asn Val Thr Gly Val
        115                 120                 125

Phe Leu Phe Met Lys His Ala Ala Arg Ile Met Val Pro Ala Arg Ser
130                 135                 140

Gly Cys Ile Ile Ser Thr Ala Ser Leu Ser Ser Thr Met Gly Gly Gly
145                 150                 155                 160

Ser Ser His Ala Tyr Cys Gly Ser Lys His Ala Val Leu Gly Leu Thr
                165                 170                 175

Arg Asn Leu Ala Val Glu Leu Gly Gln Phe Gly Ile Arg Val Asn Cys
            180                 185                 190

Leu Ser Pro Phe Gly Leu Pro Thr Pro Leu Ala Lys Lys Phe Thr Gly
        195                 200                 205

Ile Glu Asn Asp Glu Asp Leu Ala Asn Gly Ile Glu Arg Ala Gly Asn
    210                 215                 220

Leu Lys Gly Thr Lys Leu Arg Ile Glu Asp Val Ala Asn Ala Ala Leu
225                 230                 235                 240

Phe Leu Ala Ser Asp Glu Ala Gln Tyr Val Ser Gly Gln Asn Leu Phe
                245                 250                 255

Ile Asp Gly Gly Phe Ser Val Cys Asn Ser Ala Ile Lys Leu Phe Gln
            260                 265                 270

Tyr Pro Asp Ser
        275

<210> SEQ ID NO 11
<211> LENGTH: 21
<212> TYPE: PRT
<213> ORGANISM: Forsythia x intermedia
<220> FEATURE:
<221> NAME/KEY: PEPTIDE
<222> LOCATION: (1)..(21)
<223> OTHER INFORMATION: N-terminal peptide of F. intermedia
      secoisolariciresinol protein wherein Xaa at
      positions 3, 12 and 20 represents an unidentified
      amino acid residue

<400> SEQUENCE: 11

Gln Val Xaa Thr Ala Ile Ala Arg Asp Leu Glu Xaa Lys Val Ala Leu
  1               5                  10                  15

Ile Thr Gly Xaa Ala
             20
```

```
<210> SEQ ID NO 12
<211> LENGTH: 17
<212> TYPE: PRT
<213> ORGANISM: Forsythia x intermedia

<400> SEQUENCE: 12

Val Ala Leu Ile Thr Gly Gly Ala Ser Gly Ile Gly Glu Thr Thr Ala
 1               5                  10                  15
Lys

<210> SEQ ID NO 13
<211> LENGTH: 15
<212> TYPE: PRT
<213> ORGANISM: Forsythia x intermedia

<400> SEQUENCE: 13

Leu Asn Ile Met Phe Ser Asn Ala Gly Ile Ser Asp Pro Asn Lys
 1               5                  10                  15

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence:
      oligonucleotide
<220> FEATURE:
<221> NAME/KEY: misc_feature
<222> LOCATION: (1)..(20)
<223> OTHER INFORMATION: PCR primer wherein n at positions 3, 9, 15 and
      18 represents inosine

<400> SEQUENCE: 14
ggnathggng aracnacngc                                              20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence:
      oligonucleotide
<220> FEATURE:
<221> NAME/KEY: misc_feature
<222> LOCATION: (1)..(20)
<223> OTHER INFORMATION: PCR primer wherein n at positions 3 and  9
      represents inosine

<400> SEQUENCE: 15
ccngcrttng araacatdat                                              20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence:
      oligonucleotide
<220> FEATURE:
<221> NAME/KEY: misc_feature
<222> LOCATION: (1)..(20)
<223> OTHER INFORMATION: PCR primer wherein n at positions 3 and 9
      represents inosine

<400> SEQUENCE: 16
ccngcrttnc traacatdat                                              20
```

```
<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence:
      oligonucleotide
<220> FEATURE:
<221> NAME/KEY: misc_feature
<222> LOCATION: (1)..(20)
<223> OTHER INFORMATION: PCR primer

<400> SEQUENCE: 17
attccgctag attgcattga                                            20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence:
      oligonucleotide
<220> FEATURE:
<221> NAME/KEY: misc_feature
<222> LOCATION: (1)..(20)
<223> OTHER INFORMATION: PCR primer wherein n at positions 3 and 9
      represent inosine

<400> SEQUENCE: 18
ccngcrttnc traacatdat                                            20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence:
      oligonucleotide
<220> FEATURE:
<221> NAME/KEY: misc_feature
<222> LOCATION: (1)..(20)
<223> OTHER INFORMATION: T7 PCR primer

<400> SEQUENCE: 19
aattaaccct cactaaaggg                                            20

<210> SEQ ID NO 20
<211> LENGTH: 23
<212> TYPE: DNA
<213> ORGANISM: Artificial Sequence
<220> FEATURE:
<223> OTHER INFORMATION: Description of Artificial Sequence:
      oligonucleotide
<220> FEATURE:
<221> NAME/KEY: misc_feature
<222> LOCATION: (1)..(23)
<223> OTHER INFORMATION: PCR primer

<400> SEQUENCE: 20
cagcttcgaa ctgcattcgc aag                                        23

<210> SEQ ID NO 21
<211> LENGTH: 22
<212> TYPE: DNA
<213> ORGANISM: Artificial Sequence
<220> FEATURE:
<223> OTHER INFORMATION: Description of Artificial Sequence:
      oligonucleotide
```

-continued

```
<220> FEATURE:
<221> NAME/KEY: misc_feature
<222> LOCATION: (1)..(22)
<223> OTHER INFORMATION: T7 PCR primer

<400> SEQUENCE: 21
cgggatatca ctcagcataa tg                                              22

<210> SEQ ID NO 22
<211> LENGTH: 816
<212> TYPE: DNA
<213> ORGANISM: Forsythia x intermedia
<220> FEATURE:
<221> NAME/KEY: CDS
<222> LOCATION: (1)..(816)

<400> SEQUENCE: 22
```

| | | | | | | | | | | | | | | | | |
|---|---|---|---|---|---|---|---|---|---|---|---|---|---|---|---|---|
| cag | ctt | cga | act | gca | ttc | gca | aga | agg | cta | gaa | gga | aaa | gtt | gcc | ctt | 48 |
| Gln | Leu | Arg | Thr | Ala | Phe | Ala | Arg | Arg | Leu | Glu | Gly | Lys | Val | Ala | Leu | |
| 1 | | | | 5 | | | | | 10 | | | | | 15 | | |
| ata | aca | gga | gga | gcc | agt | gga | att | gga | gaa | acc | aca | gca | aaa | ctc | ttc | 96 |
| Ile | Thr | Gly | Gly | Ala | Ser | Gly | Ile | Gly | Glu | Thr | Thr | Ala | Lys | Leu | Phe | |
| | | | 20 | | | | | 25 | | | | | 30 | | | |
| tcc | caa | cat | gga | gcc | aaa | gtt | gcc | att | gct | gat | gtc | caa | gat | gaa | tta | 144 |
| Ser | Gln | His | Gly | Ala | Lys | Val | Ala | Ile | Ala | Asp | Val | Gln | Asp | Glu | Leu | |
| | 35 | | | | | 40 | | | | | 45 | | | | | |
| ggt | cac | tca | gtt | gtc | gag | gcc | att | ggc | act | tcc | aat | tcc | acc | tac | atc | 192 |
| Gly | His | Ser | Val | Val | Glu | Ala | Ile | Gly | Thr | Ser | Asn | Ser | Thr | Tyr | Ile | |
| 50 | | | | | 55 | | | | | 60 | | | | | | |
| cac | tgt | gat | gtt | act | aat | gaa | gac | ggt | gtt | aaa | aat | gcc | gtg | gac | aac | 240 |
| His | Cys | Asp | Val | Thr | Asn | Glu | Asp | Gly | Val | Lys | Asn | Ala | Val | Asp | Asn | |
| 65 | | | | | 70 | | | | | 75 | | | | | 80 | |
| aca | gtt | tca | acc | tat | gga | aaa | ctg | gac | att | atg | ttc | agc | aat | gca | gga | 288 |
| Thr | Val | Ser | Thr | Tyr | Gly | Lys | Leu | Asp | Ile | Met | Phe | Ser | Asn | Ala | Gly | |
| | | | | 85 | | | | | 90 | | | | | 95 | | |
| att | tct | gat | ccc | aac | agg | ccc | cgc | atc | ata | gac | aac | gaa | aaa | gca | gac | 336 |
| Ile | Ser | Asp | Pro | Asn | Arg | Pro | Arg | Ile | Ile | Asp | Asn | Glu | Lys | Ala | Asp | |
| | | | 100 | | | | | 105 | | | | | 110 | | | |
| ttt | gaa | cgc | gtt | ctc | agt | gta | aat | gta | acc | gga | gtt | ttc | cta | tgc | atg | 384 |
| Phe | Glu | Arg | Val | Leu | Ser | Val | Asn | Val | Thr | Gly | Val | Phe | Leu | Cys | Met | |
| | 115 | | | | | 120 | | | | | 125 | | | | | |
| aag | cac | gca | gca | cgt | gtt | atg | att | cca | gca | cgc | agt | ggc | aac | ata | att | 432 |
| Lys | His | Ala | Ala | Arg | Val | Met | Ile | Pro | Ala | Arg | Ser | Gly | Asn | Ile | Ile | |
| 130 | | | | | 135 | | | | | 140 | | | | | | |
| tcc | act | gct | agt | tta | agc | tca | act | atg | ggt | ggt | ggt | tct | tca | cat | gcc | 480 |
| Ser | Thr | Ala | Ser | Leu | Ser | Ser | Thr | Met | Gly | Gly | Gly | Ser | Ser | His | Ala | |
| 145 | | | | | 150 | | | | | 155 | | | | | 160 | |
| tat | tgt | ggt | tca | aag | cat | gct | gtg | tta | gcc | ctt | act | agg | aat | ctg | gca | 528 |
| Tyr | Cys | Gly | Ser | Lys | His | Ala | Val | Leu | Ala | Leu | Thr | Arg | Asn | Leu | Ala | |
| | | | | 165 | | | | | 170 | | | | | 175 | | |
| gtc | gag | ctc | gga | caa | ttt | ggc | att | agg | gtt | aat | tgt | ttg | tct | cct | ttc | 576 |
| Val | Glu | Leu | Gly | Gln | Phe | Gly | Ile | Arg | Val | Asn | Cys | Leu | Ser | Pro | Phe | |
| | | | 180 | | | | | 185 | | | | | 190 | | | |
| ggg | ctt | cct | acg | gct | tta | ggc | aag | aaa | ttt | tca | ggg | att | aaa | aat | gaa | 624 |
| Gly | Leu | Pro | Thr | Ala | Leu | Gly | Lys | Lys | Phe | Ser | Gly | Ile | Lys | Asn | Glu | |
| | 195 | | | | | 200 | | | | | 205 | | | | | |
| gaa | gaa | ttt | gag | aat | gta | ata | aac | ttt | gcg | gga | aat | ttg | aaa | ggt | cca | 672 |
| Glu | Glu | Phe | Glu | Asn | Val | Ile | Asn | Phe | Ala | Gly | Asn | Leu | Lys | Gly | Pro | |
| 210 | | | | | 215 | | | | | 220 | | | | | | |
| aaa | ttt | aat | gtt | gag | gat | gtt | gcc | aat | gca | gct | ctt | tat | ctg | gct | agt | 720 |
| Lys | Phe | Asn | Val | Glu | Asp | Val | Ala | Asn | Ala | Ala | Leu | Tyr | Leu | Ala | Ser | |
| 225 | | | | | 230 | | | | | 235 | | | | | 240 | |

```
gat gag gca aaa tac gtg agt gga cac aat ctg ttc att gat gga ggg    768
Asp Glu Ala Lys Tyr Val Ser Gly His Asn Leu Phe Ile Asp Gly Gly
            245                 250                 255 ttc agc gtc tgc aat tct gta atc aaa gtg ttc caa tat cca gat tct    816
Phe Ser Val Cys Asn Ser Val Ile Lys Val Phe Gln Tyr Pro Asp Ser
        260                 265                 270

<210> SEQ ID NO 23
<211> LENGTH: 272
<212> TYPE: PRT
<213> ORGANISM: Forsythia x intermedia

<400> SEQUENCE: 23

Gln Leu Arg Thr Ala Phe Ala Arg Arg Leu Glu Gly Lys Val Ala Leu
 1               5                  10                  15

Ile Thr Gly Gly Ala Ser Gly Ile Gly Glu Thr Thr Ala Lys Leu Phe
            20                  25                  30

Ser Gln His Gly Ala Lys Val Ala Ile Ala Asp Val Gln Asp Glu Leu
        35                  40                  45

Gly His Ser Val Val Glu Ala Ile Gly Thr Ser Asn Ser Thr Tyr Ile
    50                  55                  60

His Cys Asp Val Thr Asn Glu Asp Gly Val Lys Ala Val Asp Asn
 65                  70                  75                  80

Thr Val Ser Thr Tyr Gly Lys Leu Asp Ile Met Phe Ser Asn Ala Gly
                85                  90                  95

Ile Ser Asp Pro Asn Arg Pro Arg Ile Ile Asp Asn Glu Lys Ala Asp
            100                 105                 110

Phe Glu Arg Val Leu Ser Val Asn Val Thr Gly Val Phe Leu Cys Met
        115                 120                 125

Lys His Ala Ala Arg Val Met Ile Pro Ala Arg Ser Gly Asn Ile Ile
    130                 135                 140

Ser Thr Ala Ser Leu Ser Ser Thr Met Gly Gly Ser Ser His Ala
145                 150                 155                 160

Tyr Cys Gly Ser Lys His Ala Val Leu Ala Leu Thr Arg Asn Leu Ala
                165                 170                 175

Val Glu Leu Gly Gln Phe Gly Ile Arg Val Asn Cys Leu Ser Pro Phe
            180                 185                 190

Gly Leu Pro Thr Ala Leu Gly Lys Lys Phe Ser Gly Ile Lys Asn Glu
        195                 200                 205

Glu Glu Phe Glu Asn Val Ile Asn Phe Ala Gly Asn Leu Lys Gly Pro
    210                 215                 220

Lys Phe Asn Val Glu Asp Val Ala Asn Ala Ala Leu Tyr Leu Ala Ser
225                 230                 235                 240

Asp Glu Ala Lys Tyr Val Ser Gly His Asn Leu Phe Ile Asp Gly Gly
                245                 250                 255

Phe Ser Val Cys Asn Ser Val Ile Lys Val Phe Gln Tyr Pro Asp Ser
            260                 265                 270

<210> SEQ ID NO 24
<211> LENGTH: 33
<212> TYPE: DNA
<213> ORGANISM: Artificial Sequence
<220> FEATURE:
<223> OTHER INFORMATION: Description of Artificial Sequence:
      oligonucleotide
<220> FEATURE:
<221> NAME/KEY: misc_feature
<222> LOCATION: (1)..(33)
<223> OTHER INFORMATION: PCR primer
```

-continued

```
<400> SEQUENCE: 24
acatatgcag cttcgaactg cattcgcaag aag                          33

<210> SEQ ID NO 25
<211> LENGTH: 33
<212> TYPE: DNA
<213> ORGANISM: Artificial Sequence
<220> FEATURE:
<223> OTHER INFORMATION: Description of Artificial Sequence:
      oligonucleotide
<220> FEATURE:
<221> NAME/KEY: misc_feature
<222> LOCATION: (1)..(33)
<223> OTHER INFORMATION: PCR primer

<400> SEQUENCE: 25
catatgggca gacatgttac atgatcaatt gca                          33
```

RECOMBINANT SECOISOLARICICIRESINOL DEHYDROGENSASE, AND METHODS OF USE

CROSS-REFERENCE TO RELATED APPLICATION

This application claims the benefit of Provisional Application No. 60/082,977, filed Apr. 24, 1998.

FIELD OF THE INVENTION

The present invention relates to isolated secoisolariciresinol dehydrogenase proteins, to nucleic acid sequences which code for secoisolariciresinol dehydrogenase proteins, and to vectors containing the sequences, host cells containing the sequences and methods of producing recombinant secoisolariciresinol dehydrogenase proteins and their mutants.

BACKGROUND OF THE INVENTION

Lignans are a large, structurally diverse, class of vascular plant metabolites having a wide range of physiological functions and pharmacologically important properties (Ayres, D. C., and Loike, J. D. in *Chemistry and Pharmacology of Natural Products*. Lignans. Chemical, Biological and Clinical Properties, Cambridge University Press, Cambridge, England (1990); Lewis et al., in Chemistry of the Amazon, Biodiversity Natural Products, and Environmental Issues, 588, (P. R. Seidl, O. R. Gottlieb and M. A. C. Kaplan) 135–167, ACS Symposium Series, Washington D.C. (1995)). Because of their pronounced antibiotic properties (Markkanen, T. et al., *Drugs Exptl. Clin. Res.* 7:711–718 (1981)), antioxidant properties (Fauré, M. et al., *Phytochemistry* 29:3773–3775 (1990); Osawa, T. et al., *Agric. Biol. Chem.* 49:3351–3352 (1985)) and antifeedant properties (Harmatha, J., and Nawrot, J., *Biochem. Syst. Ecol.* 12:95–98 (1984)), a major role of lignans in vascular plants is to help confer resistance against various opportunistic biological pathogens and predators. Lignans have also been proposed as cytokinins (Binns, A. N. et al., *Proc. Natl. Acad Sci. USA* 84:980–984 (1987)) and as intermediates in lignification (Rahman, M. M. A. et al., *Phytochemistry* 29:1861–1866 (1990)), suggesting a critical role in plant growth and development. It is widely held that elaboration of biochemical pathways to lignins/lignans and related substances from phenylalanine (tyrosine) was essential for the successful transition of aquatic plants to their vascular dry-land counterparts (Lewis, N. G., and Davin, L. B., in *Isoprenoids and Other Natural Products. Evolution and Function*, 562 (W. D. Nes, ed) 202–246, ACS Symposium Series: Washington, D.C. (1994)), some four hundred and eighty million years ago (Graham, L. E., *Origin of Land Plants*, John Wiley & Sons, Inc., New York, N.Y. (1993)).

Based on existing chemotaxonomic data, lignans are present in "primitive" plants, such as the fern *Blechnum orientale* (Wada, H. et al., *Chem. Pharm. Bull.* 40:2099–2101 (1992)) and the hornworts, e. g., *Dendroceros japonicus* and *Megaceros flagellaris* (Takeda, R. et al., in *Bryophytes. Their Chemistry and Chemical Taxonomy*, Vol. 29 (Zinsmeister, H. D. and Mues, R. eds) pp. 201–207, Oxford University Press: New York, N.Y. (1990); Takeda, R. et al., *Tetrahedron Lett.* 31:4159–4162 (1990)), with the latter recently being classified as originating in the Silurian period (Graham, L. E., *J. Plant Res.* 109: 241–252 (1996)). Interestingly, evolution of both gymnosperms and angiosperms was accompanied by major changes in the structural complexity and oxidative modifications of the lignans (Lewis, N. G., and Davin, L. B., in *Isoprenoids and Other Natural Products. Evolution and Function*, 562 (W. D. Nes, ed. ) 202–246, ACS Symposium Series: Washington, D.C. (1994); Gottlieb, O. R., and Yoshida, M., in *Natural Products of Woody Plants. Chemicals Extraneous to the Lignocellulosic Cell Wall* (Rowe, J. W. and Kirk, C. H. eds.) pp. 439–511, Springer Verlag: Berlin (1989)). Indeed, in some species, such as Western Red Cedar (*Thuja plicata*), lignans can contribute extensively to heartwood formation/generation by enhancing the resulting heartwood color, quality, fragrance and durability.

In addition to their functions in plants, lignans also have important pharmacological roles. For example, podophyllotoxin, as its etoposide and teniposide derivatives, is an example of a plant compound that has been successfully employed as an anticancer agent (Ayres, D. C., and Loike, J. D. in *Chemistry and Pharmacology of Natural Products*. Lignans. Chemical, Biological and Clinical Properties, Cambridge University Press, Cambridge, England (1990)). Antiviral properties have also been reported for selected lignans. For example, (−)-arctigenin (Schröder, H. C. et al., *Z. Naturforsch* 45c, 1215–1221 (1990)), (−)-trachelogenin (Schröder, H. C. et al., *Z. Naturforsch.* 45c, 1215–1221 (1990)) and nordihydroguaiaretic acid (Gnabre, J. N. et al., *Proc. Natl. Acad Sci. USA* 92:11239–11243 (1995)) are each effective against HIV due to their pronounced reverse transcriptase inhibitory activities. Some lignans, e. g., matairesinol (Nikaido, T. et al., *Chem. Pharm. Bull.* 29:3586–3592 (1981)), inhibit cAMP-phosphodiesterase, whereas others enhance cardiovascular activity, e. g., syringaresinol β-D-glucoside (Nishibe, S. et al., *Chem. Pharm. Bull.* 38:1763–1765 (1990)). There is also a high correlation between the presence, in the diet, of the "mammalian" lignans or "phytoestrogens", enterolactone and enterodiol, formed following digestion of high fiber diets, and reduced incidence rates of breast and prostate cancers (so-called chemoprevention) (Axelson, M., and Setchell, K. D. R, *FEBS Lett.* 123:337–342 (1981); Adlercreutz et al., *J. Steroid Biochem. Molec. Biol.* 41:3–8 (1992); Adlercreutz et al., *J. Steroid Biochem. Molec. Biol.* 52:97–103 (1995)). The "mammalian lignans," in turn, are considered to be derived from lignans such as matairesinol and secoisolariciresinol (Boriello et al., *J. Applied Bacteriol.*, 58:37–43 (1985)).

The biosynthetic pathways to the lignans are only now being defined. Based on radiolabeling experiments with crude enzyme extracts from *Forsythia intermedia*, it was first established that entry into the 8,8'-linked lignans, which represent the most prevalent dilignol linkage known (Davin, L. B., and Lewis, N. G., in *Rec. Adv. Phytochemistry*, Vol. 26 (Stafford, H. A., and Ibrahim, R. K., eds), pp. 325–375, Plenum Press, New York, N.Y. (1992)), occurs via stereoselective coupling of two achiral coniferyl alcohol molecules, in the form of oxygenated free radicals, to afford the furofuran lignan (+)-pinoresinol (Davin, L. B., Bedgar, D. L., Katayama, T., and Lewis, N. G., *Phytochemistry* 31:3869–3874 (1992); Paré, P. W. et al., *Tetrahedron Lett.* 35:4731–4734 (1994)).

Recently, the initial step in the 8-8' linked lignan biosynthetic pathway was clarified in *F. intermedia* (Davin, L. B., Wang, H.-B., Crowell, A. L., Bedgar, D. L., Martin, D. M., Sarkanen, S., Lewis, N. G., *Science* 275:362–366 (1997)). This involved stereoselective monolignol coupling of two molecules of coniferyl alcohol in the presence of a 78 kDa dirigent protein and a one-electron oxidase (such as laccase). The one-electron oxidant is considered only to provide oxidative capacity, with the dirigent protein binding, orientating, and coupling the free-radical forms and releasing (+)-pinoresinol. The dirigent protein was purified from *F. intermedia* stem tissue and its encoding gene cloned (Gang, D. R., Costa, M. A., Fujita, M., Dinkova-Kostova, A. T., Wang, H. B., Burlat, V., Martin, W., Sarkanen, S., Davin, L. B., Lewis, N. G., *Chemistry & Biology* 6:143–151(1999)).

In *Forsythia intermedia*, and presumably other species, (+)-pinoresinol undergoes sequential reduction to generate (+)-lariciresinol and then (−)-secoisolariciresinol (Katayama, T. et al., *Phytochemistry* 32:581–591 (1993); Chu, A. et al., *J. Biol. Chem.* 268:27026–27033 (1993)). The reductions catalyzed by pinoresinol/lariciresinol reductase proceed via abstraction of the pro-R hydride of NADPH, resulting in an "inversion" of configuration at both the C-7 and C-7' positions of the products, (+)-lariciresinol and (−)-secoisolariciresinol (Chu, A., et al., *J. Biol. Chem.* 268:27026–27033 (1993)). Pinoresinol/lariciresinol reductase was purified ~3200 fold to apparent electrophoretic homogeneity from a soluble crude protein extract; this was achieved by employing a series of affinity, hydrophobic interaction, hydroxyapatite, gel filtration, and ion exchange chromatographic steps (Dinkova-Kostova, A. T., Gang, D. R., Davin, L. B., Bedgar, D. L., Chu, A., Lewis, N. G., *J. Biol. Chem.* 271:29473–29482 (1996)). The purified protein was demonstrated to be a type A NADPH-dependent reductase.

The corresponding pinoresinol/lariciresinol reductase gene (called plr-Fi1) was cloned from a *Forsythia* cDNA library (Dinkova-Kostova, A. T., Gang, D. R., Davin, L. B., Bedgar, D. L., Chu, A., Lewis, N. G., *J. Biol. Chem.* 271:29473–29482 (1996)), and its fully functional recombinant protein then over-expressed in *E. coli* using a pET-based expression system (pSBETa vector) (Schenk, P. M., Baumann, S., Mattes, R., Steinbiβ, H.-H., *BioTechniques* 19:196–200 (1995)). It was found that the only products formed following incubation of the recombinant pinoresinol/lariciresinol reductase with (±)-pinoresinols in the presence of NADPH were (+)-lariciresinol and (−)-secoisolariciresinol, i. e., only (+)-pinoresinol and (+)-lariciresinol, and not (−)-pinoresinol nor (−)-lariciresinol, served as substrates. Thus, the recombinant enzyme catalyzed exactly the same enantiospecific conversion as for the native plant protein from *Forsythia* (Dinkova-Kostova, A. T., Gang, D. R., Davin, L. B., Bedgar, D. L., Chu, A., Lewis, N. G., *J. Biol. Chem.* 271:29473–29482 (1996); Lewis, N. G., Davin, L. B., in: *Comprehensive Natural Products Chemistry*, Vol. 1. (Barton, Sir D. H. R., Nakanishi, K., and Meth-Cohn, O., eds), pp 639–712, Elsevier, London (1999)). (−)-Matairesinol is subsequently formed via dehydrogenation of (−)-secoisolariciresinol, further metabolism of which presumably affords lignans such as the antiviral (−)-trachelogenin in *Ipomoea cairica* and (−)-podophyllotoxin in *Podophyllum peltatum*.

Thus, the stereospecific formation of (+)-pinoresinol and the subsequent reductive steps giving (+)-lariciresinol and (−)-secoisolariciresinol are pivotal points in lignan metabolism, since they represent entry into the furano, dibenzylbutane, dibenzylbutyrolactone and aryltetrahydronaphthalene lignan subclasses. Additionally, it should be noted that while lignans are normally optically active, the particular enantiomer present may differ between plant species. For example, (−)-pinoresinol occurs in *Xanthoxylum ailanthoides* (Ishii et al., *Yakugaku Zasshi*, 103:279–292 (1983)), and (−)-lariciresinol is present in *Daphne tangutica* (Lin-Gen, et al., *Planta Medica*, 45:172–176 (1982)). The optical activity of a particular lignan may have important ramifications regarding biological activity. For example, (−)-trachelogenin inhibits the in vitro replication of HIV-1, whereas its (+)-enantiomer is much less effective (Schroder et al., *Naturforsch.* 45c:1215–1221(1990)).

The lignan, matairesinol, is an important component of the plant arsenal that helps confer dietary benefits to humans, specifically against the onset of breast and prostate cancers (Adlercruetz, H. and Mazur, W. *Anal. Med.*, 1997, 29:95–120). This lignan is found in various whole-grain cereal food, seed and berries, and is converted by intestinal bacteria to form enterolactone; the latter compound is considered to be the primary metabolite in conferring the health protection. Additionally, the lignan, matairesinol, also has an important function in conferring quality, color and durability to specific heartwoods, such as the highly valued western red cedar (*Thuja plicata*) species via its conversion into plicatic acid and its congeners. Using *Forsythia intermedia* as a model system, it was established that matairesinol is formed in planta via dehydrogenation of secoisolariciresinol (FIG. 1) (Umezawa, T., Davin, L. B. and Lewis, N. G., *Biochem. Biophys. Res. Commun.*, 1990, 171(3), 1008–1014; Umezawa, T., Davin, L. B., Kingston, D. G. I., Yamamoto, E. and Lewis, N. G., *J. Chem. Soc., Chem. Commun.*, 1990, 1405–1408; Umezawa, T., Davin, L. B. and Lewis, N. G., *J. Biol. Chem.*, 1991, 266:10210–10217).

SUMMARY OF THE INVENTION

In accordance with the foregoing, a secoisolariciresinol dehydrogenase protein has been purified from *Forsythia intermedia*. Thus, one aspect of the invention relates to isolated recombinant secoisolariciresinol dehydrogenase proteins, such as, for example, that from *Forsythia intermedia*. Presently preferred, isolated recombinant, secoisolariciresinol dehydrogenase proteins of the present invention correspond to secoisolariciresinol dehydrogenase proteins that occur naturally in an angiosperm or gymnosperm plant species; have a molecular weight of from about 27 kDa to about 31 kDa, more preferably about 29 kDa; an isoelectric point of from about 5.9 to about 6.85, and require NAD or NADP as a cofactor.

In other aspects of the invention, cDNAs encoding secoisolariciresinol dehydrogenase from *Forsythia intermedia* have been isolated and sequenced, and the corresponding amino acid sequences have been deduced. Accordingly, the present invention relates to isolated DNA sequences which code for the expression of secoisolariciresinol dehydrogenase, such as the sequences designated SEQ ID NO:1, SEQ ID NO:3, SEQ ID NO:5, SEQ ID NO:7, SEQ ID NO:9, which encode secoisolariciresinol dehydrogenase proteins designated SEQ ID NO:2, SEQ ID NO:4, SEQ ID NO:6, SEQ ID NO:8 and SEQ ID NO:10, respectively, from *Forsythia intermedia*. Presently preferred DNA sequences encoding secoisolariciresinol dehydrogenase are isolated from a gymnosperm or angiosperm plant species.

In another aspect, the present invention is directed to isolated nucleic acid molecules that hybridize under stringent hybridization conditions to a fragment (having a length of at least 15 bases) of any one of the nucleic acid molecules having the nucleic acid sequences set forth in SEQ ID NO:1, SEQ ID NO:3, SEQ ID NO:5, SEQ ID NO:7 and SEQ ID NO:9.

Thus, the present invention relates to isolated proteins and to isolated DNA sequences which code for the expression of secoisolariciresinol dehydrogenase. In other aspects, the present invention is directed to replicable recombinant cloning vehicles comprising a nucleic acid sequence which codes for a secoisolariciresinol dehydrogenase protein. The present invention is also directed to a base sequence sufficiently complementary to at least a portion of a secoisolariciresinol dehydrogenase DNA or RNA to enable hybridization therewith. The aforesaid complementary base sequences include, but are not limited to: antisense secoisolariciresinol dehydrogenase RNA; fragments of DNA that are complementary to a secoisolariciresinol dehydrogenase DNA, and which are therefore useful as polymerase chain reaction primers, or as probes for secoisolariciresinol dehydrogenase genes, or related genes.

In yet other aspects of the invention, modified host cells are provided that have been transformed, transfected, infected and/or injected with a recombinant cloning vehicle and/or DNA sequence of the invention. Thus, the present invention provides for the recombinant expression of secoisolariciresinol dehydrogenase in plants, animals, microbes and in cell cultures. The inventive concepts described herein may be used, for example, to facilitate the production, isolation and purification of significant quantities of recombinant secoisolariciresinol dehydrogenase, or of its enzyme products, in plants, animals, microbes or cell cultures.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

Figure 1:
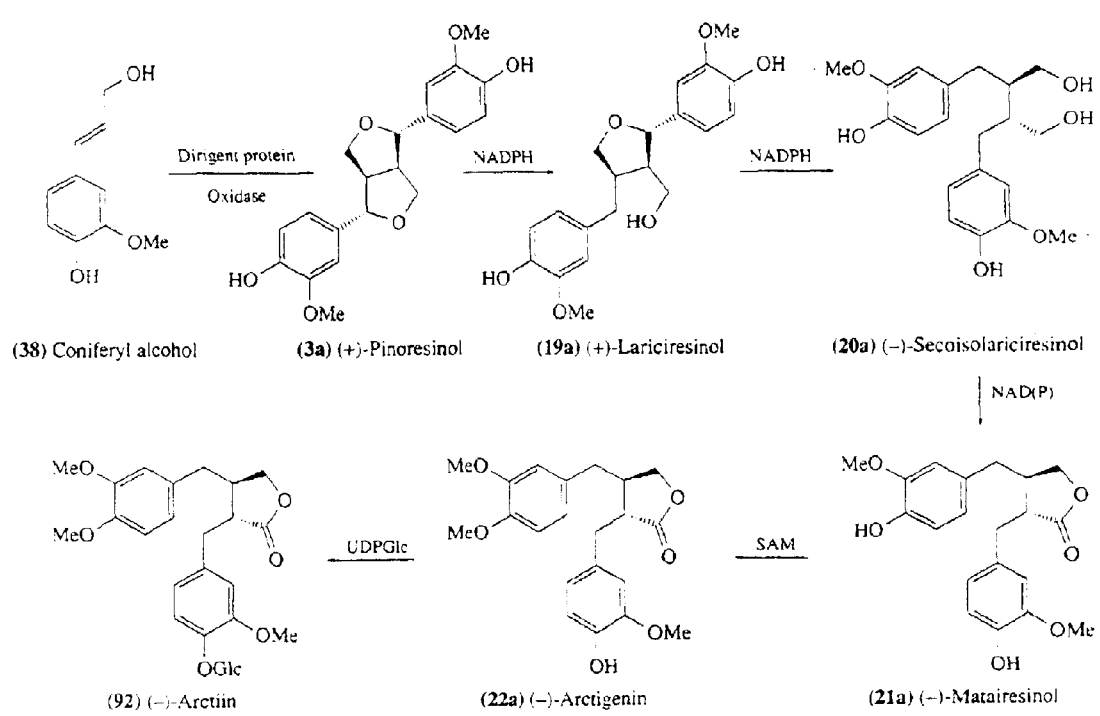
FIG. 1 shows the enzymatic conversion of (−)-secoisolariciresinol (structure on the left) to (−)-matairesinol (structure on the right) via (−) lactol (structure in the middle).

FIG. (B) shows the mode of action of recombinant secoisolariciresinol dehydrogenase. (±)-[9,9-$^3$H] secoisolariciresinols were incubated with secoisolariciresinol dehydrogenase. The resulting matairesinol product formed was chemically reduced and subjected to HPLC chiral column [Chiralcel OD, Daicel] analysis. This analysis revealed that only the (−)-antipode was present as evidenced by chiral column analysis of the chemically reduced product, (−)-secoisolariciresinol. Therefore the enzymatic reduction was entirely enantiospecific.

DETAILED DESCRIPTION OF THE PREFERRED EMBODIMENT

As used herein, the terms "amino acid" and "amino acids" refer to all naturally occurring L-α-amino acids or their residues. The amino acids are identified by either the single-letter or three-letter designations:

| Asp | D | aspartic acid | Ile | I | isoleucine |
|---|---|---|---|---|---|
| Thr | T | threonine | Leu | L | leucine |
| Ser | S | serine | Tyr | Y | tyrosine |
| Glu | E | glutamic acid | Phe | F | phenylalanine |
| Pro | P | proline | His | H | histidine |
| Gly | G | glycine | Lys | K | lysine |
| Ala | A | alanine | Arg | R | arginine |
| Cys | C | cysteine | Trp | W | tryptophan |
| Val | V | valine | Gln | Q | glutamine |
| Met | M | methionine | Asn | N | asparagine |

As used herein, the term "nucleotide" means a monomeric unit of DNA or RNA containing a sugar moiety (pentose), a phosphate and a nitrogenous heterocyclic base. The base is linked to the sugar moiety via the glycosidic carbon (1' carbon of pentose) and that combination of base and sugar is called a nucleoside. The base characterizes the nucleotide with the four bases of DNA being adenine ("A"), guanine ("G"), cytosine ("C") and thymine ("T"). Inosine ("I") is a synthetic base that can be used to substitute for any of the four, naturally-occurring bases (A, C, G or T). The four RNA bases are A,G,C and uracil ("U"). The nucleotide sequences described herein comprise a linear array of nucleotides connected by phosphodiester bonds between the 3' and 5' carbons of adjacent pentoses.

"Oligonucleotide" refers to short length single or double stranded sequences of deoxyribonucleotides linked via phosphodiester bonds. The oligonucleotides are chemically synthesized by known methods and purified, for example, on polyacrylamide gels.

The terms "alteration", "amino acid sequence alteration", "variant" and "amino acid sequence variant" refer to secoisolariciresinol dehydrogenase molecules with some differences in their amino acid sequences as compared to the corresponding native secoisolariciresinol dehydrogenase. Ordinarily, the variants will possess at least about 70% homology with the corresponding, native secoisolariciresinol dehydrogenase, and preferably they will be at least about 80% homologous with the corresponding, native secoisolariciresinol dehydrogenase. The amino acid sequence variants of secoisolariciresinol dehydrogenase falling within this invention possess substitutions, deletions, and/or insertions at certain positions. Sequence variants of secoisolariciresinol dehydrogenase may be used to attain desired enhanced or reduced enzymatic activity, modified regiochemistry or stereochemistry, or altered substrate utilization or product distribution.

Substitutional secoisolariciresinol dehydrogenase variants are those that have at least one amino acid residue in the corresponding native secoisolariciresinol dehydrogenase sequence removed and a different amino acid inserted in its place at the same position. The substitutions may be single, where only one amino acid in the molecule has been substituted, or they may be multiple, where two or more amino acids have been substituted in the same molecule. Substantial changes in the activity of the secoisolariciresinol dehydrogenase molecule may be obtained by substituting an amino acid with a side chain that is significantly different in charge and/or structure from that of the native amino acid. This type of substitution would be expected to affect the structure of the polypeptide backbone and/or the charge or hydrophobicity of the molecule in the area of the substitution.

Moderate changes in the activity of the secoisolariciresinol dehydrogenase molecule would be expected by substituting an amino acid with a side chain that is similar in charge and/or structure to that of the native molecule. This type of substitution, referred to as a conservative substitution, would not be expected to substantially alter either the structure of the polypeptide backbone or the charge or hydrophobicity of the molecule in the area of the substitution.

Insertional secoisolariciresinol dehydrogenase variants are those with one or more amino acids inserted immediately adjacent to an amino acid at a particular position in the native secoisolariciresinol dehydrogenase molecule. Immediately adjacent to an amino acid means connected to either the α-carboxy or α-amino functional group of the amino acid. The insertion may be one or more amino acids.

Ordinarily, the insertion will consist of one or two conservative amino acids. Amino acids similar in charge and/or structure to the amino acids adjacent to the site of insertion are defined as conservative. Alternatively, this invention includes insertion of an amino acid with a charge and/or structure that is substantially different from the amino acids adjacent to the site of insertion.

Deletional variants are those where one or more amino acids in the native secoisolariciresinol dehydrogenase molecule have been removed. Ordinarily, deletional variants will have one or two amino acids deleted in a particular region of the secoisolariciresinol dehydrogenase molecule.

Amino acid sequence variants of secoisolariciresinol dehydrogenase may have desirable altered biological activity including, for example, altered reaction kinetics, substrate utilization, product distribution or other characteristics such as regiochemistry and stereochemistry.

The term "antisense" or "antisense RNA" or "antisense nucleic acid" is used herein to mean a nucleic acid molecule that is complementary to all or part of a messenger RNA molecule. Antisense nucleic acid molecules are typically used to inhibit the expression, in vivo, of complementary, expressed messenger RNA molecules.

The terms "DNA sequence encoding", "DNA encoding" and "nucleic acid encoding" refer to the order or sequence of deoxyribonucleotides along a strand of deoxyribonucleic acid. The order of these deoxyribonucleotides determines the order of amino acids along the translated polypeptide chain. The DNA sequence thus codes for the amino acid sequence.

The terms "replicable expression vector" and "expression vector" refer to a piece of DNA, usually double-stranded, which may have inserted into it a piece of foreign DNA. Foreign DNA is defined as heterologous DNA, which is DNA not naturally found in the host. The vector is used to transport the foreign or heterologous DNA into a suitable host cell. Once in the host cell, the vector can replicate independently of or coincidentally with the host chromosomal DNA, and several copies of the vector and its inserted (foreign) DNA may be generated. In addition, the vector contains the necessary elements that permit translating the foreign DNA into a polypeptide. Many molecules of the polypeptide encoded by the foreign DNA can thus be rapidly synthesized.

The terms "transformed host cell," "transformed" and "transformation" refer to the introduction of DNA into a cell. The cell is termed a "host cell", and it may be a prokaryotic or a eukaryotic cell. Typical prokaryotic host cells include various strains of *E. coli*. Typical eukaryotic host cells are plant cells, such as maize cells, yeast cells, insect cells or animal cells. The introduced DNA is usually in the form of a vector containing an inserted piece of DNA. The introduced DNA sequence may be from the same species as the host cell or from a different species from the host cell, or it may be a hybrid DNA sequence, containing some foreign DNA and some DNA derived from the host species.

The abbreviation "SSC" refers to a buffer used in nucleic acid hybridization solutions. One liter of the 20x (twenty times concentrate) stock SSC buffer solution (pH 7.0) contains 175.3 g sodium chloride and 88.2 g sodium citrate.

In accordance with the present invention, secoisolariciresinol dehydrogenase protein from *Forsythia intermedia* has been purified to apparent homogeneity via a >6,000 fold purification using a combination of ammonium sulfate precipitation, DEAE-cellulose, ADP-sepharose, and Mono P (HR 5/20) chromatography and columns. The N-terminus of the purified secoisolariciresinol dehydrogenase protein was sequenced to obtain the N-terminal sequence (SEQ ID NO:11). Tryptic fragments of the purified secoisolariciresinol dehydrogenase protein were isolated and sequenced (SEQ ID NO:12 (peptide 1) and SEQ ID NO:13 (peptide 2)).

The N-terminal (SEQ ID NO:11) and internal peptide amino acid sequences (SEQ ID NO:12 and SEQ ID NO:13) were used to construct degenerate oligonucleotide primers. Primer DEHYF26 (SEQ ID NO:14) was constructed based on the amino acid sequence of peptide 1 having the amino acid sequence set forth in SEQ ID NO:12. Primers DEHYF30RevA (SEQ ID NO:15) and DEHYF30RevB (SEQ ID NO:16) were each constructed based on the amino acid sequence of peptide 2 having the amino acid sequence set forth in SEQ ID NO:13. Purified *F. intermedia* cDNA library DNA (2 ng) was used as the template in PCR amplification reactions with primer DEHYF26 (SEQ ID NO:14) and either primer DEHYF30RevA (SEQ ID NO:15) or primer DEHY30RevB (SEQ ID NO:16). A 200 bp fragment of the resulting PCR product was used as a probe to screen the *F. intermedia* cDNA library. One positive signal was obtained from this screening, but this clone was estimated to be truncated at the N-terminal end by approximately 60 amino acid residues, as was indicated by comparison to the original N-terminal sequence analysis of (−)-secoisolariciresinol dehydrogenase.

A primer, DEHY19REV (SEQ ID NO:17), was made from the 3' end of the truncated clone and used with the original *Forsythia* cDNA library purified phage DNA as template, but failed to yield cDNA clones having the complete N-terminus. Consequently, another primer, DEHYF30REVB (SEQ ID NO:18), was synthesized from the 3' end of the truncated clone and used with the T3 primer (SEQ ID NO:19) in a PCR with the original *Forsythia* cDNA library purified phage DNA as template. This PCR product, when cloned into TA vector, resulted in a clone having the complete N-terminus which was obtained from the initial amino acid sequencing of the blotted protein (SEQ ID NO:11). A new primer, DEHYNTERM1 (SEQ ID NO:20), made from the N-terminal DNA sequence of this clone was used with the T7 primer (SEQ ID NO:21) and again with the original purified *Forsythia* cDNA library as template. The resulting PCR band of 1 kb was purified on an agarose gel, eluted by using a Microcon 30 (AMICON) and cloned directly into a TA vector (Invitrogen). This provided a clone (DEHY130) (SEQ ID NO:22) which had the DNA sequence containing the complete N-terminal amino acid sequence present in the original protein (SEQ ID NO:11). The amino acid sequence (SEQ ID NO:23) encoded by DEHY130 (SEQ ID NO:22) was lacking a start methionine. A new 5(primer, designated DEHY130NTERM (SEQ ID NO:24), was synthesized to include a start methionine at the beginning of the sequence. Also, the 5' primer (SEQ ID NO:24) and a 3' primer, designated DEHY130CTERM (SEQ ID NO:25), were designed to incorporate Nde I restriction enzyme sites at both ends of the clone for future insertion into the SBET expression vector for production of the protein in *E. coli*. The resulting PCR product of approximately 859 bp (SEQ ID NO:1), designated DEHY133, was cloned directly into a TA vector (Invitrogen). The DNA sequence indicated that the DEHY133 dehydrogenase clone (SEQ ID NO:1) now contained a Met start codon.

In addition, the Nde I fragment from the engineered DEHY133 clone (SEQ ID NO:1) was used as a probe to re-screen 300,000 pfu from the original *F. intermedia* cDNA library. This resulted in the isolation of additional secoisolariciresinol dehydrogenase clones. The nucleic acid sequences of four of these clones are set forth in: SEQ ID NO:3 (designated SMDEHY321), SEQ ID NO:5 (designated SMDEHY431), SEQ ID NO:7 (designated SMDEHY511), SEQ ID NO:9 (designated SMDEHY631). Some of these clones, such as SMDEHY321 (SEQ ID NO:3) and SMDEHY631 (SEQ ID NO:9) produced proteins in *E. coli* that catalyzed the stereochemical conversion of (−)-secoisolariciresinol into (−)-matairesinol.

The isolation of cDNAs encoding secoisolariciresinol dehydrogenase permits the development of an efficient expression system for this functional enzyme; provides useful tools for examining the developmental regulation of lignan biosynthesis and permits the isolation of other secoisolariciresinol dehydrogenases. The isolation of the secoisolariciresinol dehydrogenase cDNAs also permits the transformation of a wide range of organisms in order to enhance or modify lignan biosynthesis.

By way of non-limiting examples, the proteins and nucleic acids of the present invention can be utilized to: elevate or otherwise alter the levels of health-protecting lignans, including phytoestrogens such as enterolactone and enterodiol, in plant species, including but not limited to vegetables, grains and fruits, and to food items incorporating material derived from such genetically altered plants; genetically alter plant species to provide an abundant, natural supply of lignans useful for a variety of purposes, for example as neutriceuticals and dietary supplements; to genetically alter living organisms to produce an abundant supply of optically pure lignans having desirable biologicalproperties, for example (−)-trachelogenin which possesses antiviral properties, and (−)-podophyllotoxin.

N-terminal transport sequences well known in the art (see, e. g., von Heijne, G. et al., *Eur. J. Biochem* 180:535–545 (1989); Stryer, *Biochemistry* W. H. Freeman and Company, New York, N.Y., p. 769 (1988)) may be employed to direct secoisolariciresinol dehydrogenase protein to a variety of cellular or extracellular locations.

Sequence variants of wild-type secoisolariciresinol dehydrogenase clones that can be produced by deletions, substitutions, mutations and/or insertions are intended to be within the scope of the invention except insofar as limited by the prior art. Secoisolariciresinol dehydrogenase amino acid sequence variants may be constructed by mutating the DNA sequence that encodes wild-type secoisolariciresinol dehydrogenase, such as by using techniques commonly referred to as site-directed mutagenesis. Various polymerase chain reaction (PCR) methods now well known in the field, such as a two primer system like the Transformer Site-Directed Mutagenesis kit from Clontech, may be employed for this purpose.

Following denaturation of the target plasmid in this system, two primers are simultaneously annealed to the plasmid; one of these primers contains the desired site-directed mutation, the other contains a mutation at another point in the plasmid resulting in elimination of a restriction site. Second strand synthesis is then carried out, tightly linking these two mutations, and the resulting plasmids are transformed into a mutS strain of *E. coli*. Plasmid DNA is isolated from the transformed bacteria, restricted with the relevant restriction enzyme (thereby linearizing the unmutated plasmids), and then retransformed into *E. coli*. This system allows for generation of mutations directly in an expression plasmid, without the necessity of subcloning or generation of single-stranded phagemids. The tight linkage of the two mutations and the subsequent linearization of unmutated plasmids results in high mutation efficiency and allows minimal screening. Following synthesis of the initial restriction site primer, this method requires the use of only one new primer type per mutation site. Rather than prepare each positional mutant separately, a set of "designed degenerate" oligonucleotide primers can be synthesized in order to introduce all of the desired mutations at a given site simultaneously. Transformants can be screened by sequencing the plasmid DNA through the mutagenized region to identify and sort mutant clones. Each mutant DNA can then be restricted and analyzed by electrophoresis on Mutation Detection Enhancement gel (J. T. Baker) to confirm that no other alterations in the sequence have occurred (by band shift comparison to the unmutagenized control).

The verified mutant duplexes can be cloned into a replicable expression vector, if not already cloned into a vector of this type, and the resulting expression construct used to transform *E. coli*, such as strain *E. coli* BL21(DE3)pLysS, for high level production of the mutant protein, and subsequent purification thereof. The method of FAB-MS mapping can be employed to rapidly check the fidelity of mutant expression. This technique provides for sequencing segments throughout the whole protein and provides the necessary confidence in the sequence assignment. In a mapping experiment of this type, protein is digested with a protease (the choice will depend on the specific region to be modified since this segment is of prime interest and the remaining map should be identical to the map of unmutagenized protein). The set of cleavage fragments is fractionated by microbore HPLC (reversed phase or ion exchange, again depending on the specific region to be modified) to provide several peptides in each fraction, and the molecular weights of the peptides are determined by FAB-MS. The masses are then compared to the molecular weights of peptides expected from the digestion of the predicted sequence, and the correctness of the sequence quickly ascertained. Since this mutagenesis approach to protein modification is directed, sequencing of the altered peptide should not be necessary if the MS agrees with prediction. If necessary to verify a changed residue, CAD-tandem MS/MS can be employed to sequence the peptides of the mixture in question, or the target peptide purified for subtractive Edman degradation or carboxypeptidase Y digestion depending on the location of the modification.

In the design of a particular site directed mutant, it is generally desirable to first make a non-conservative substitution (e. g., Ala for Cys, His or Glu) and determine if activity is greatly impaired as a consequence. The properties of the mutagenized protein are then examined with particular attention to the kinetic parameters of $K_m$ and $k_{cat}$ as sensitive indicators of altered function, from which changes in binding and/or catalysis per se may be deduced by comparison to the native enzyme. If the residue is by this means demonstrated to be important by activity impairment, or knockout, then conservative substitutions can be made, such as Asp for Glu to alter side chain length, Ser for Cys, or Arg for His. For hydrophobic segments, it is largely size that will be altered, although aromatics can also be substituted for alkyl side chains. Changes in the normal product distribution can indicate which step(s) of the reaction sequence have been altered by the mutation.

Other site directed mutagenesis techniques may also be employed with the nucleotide sequences of the invention. For example, restriction endonuclease digestion of DNA followed by ligation may be used to generate secoisolariciresinol dehydrogenase deletion variants, as described in Section 15.3 of Sambrook et al. (*Molecular Cloning: A Laboratory Manual,* 2nd Ed., Cold Spring Harbor Laboratory Press, New York, N.Y. (1989)). A similar strategy may be used to construct insertion variants, as described in Section 15.3 of Sambrook et al., supra.

Oligonucleotide-directed mutagenesis may also be employed for preparing substitution variants of this invention. It may also be used to conveniently prepare the deletion and insertion variants of this invention. This technique is well known in the art as described by Adelman et al. (*DNA* 2:183 (1983)). Generally, oligonucleotides of at least 25 nucleotides in length are used to insert, delete or substitute two or more nucleotides in the secoisolariciresinol dehydrogenase gene. An optimal oligonucleotide will have 12 to 15 perfectly matched nucleotides on either side of the nucleotides coding for the mutation. To mutagenize the wild-type secoisolariciresinol dehydrogenase, the oligonucleotide is annealed to the single-stranded DNA template molecule under suitable hybridization conditions. A DNA polymerizing enzyme, usually the Klenow fragment of *E. coli* DNA polymerase I, is then added. This enzyme uses the oligonucleotide as a primer to complete the synthesis of the mutation-bearing strand of DNA. Thus, a heteroduplex molecule is formed such that one strand of DNA encodes the wild-type secoisolariciresinol dehydrogenase inserted in the vector, and the second strand of DNA encodes the mutated form of secoisolariciresinol dehydrogenase inserted into the same vector. This beteroduplex molecule is then transformed into a suitable host cell.

Mutants with more than one amino acid substituted may be generated in one of several ways. If the amino acids are located close together in the polypeptide chain, they may be mutated simultaneously using one oligonucleotide that codes for all of the desired amino acid substitutions. If however, the amino acids are located some distance from each other (separated by more than ten amino acids, for example) it is more difficult to generate a single oligonucleotide that encodes all of the desired changes. Instead, one of two alternative methods may be employed. In the first method, a separate oligonucleotide is generated for each amino acid to be substituted. The oligonucleotides are then annealed to the single-stranded template DNA simultaneously, and the second strand of DNA that is synthesized from the template will encode all of the desired amino acid substitutions.

An alternative method involves two or more rounds of mutagenesis to produce the desired mutant. The first round is as described for the single mutants: wild-type secoisolariciresinol dehydrogenase DNA is used for the template, an oligonucleotide encoding the first desired amino acid substitution(s) is annealed to this template, and the heteroduplex DNA molecule is then generated. The second round of mutagenesis utilizes the mutated DNA produced in the first round of mutagenesis as the template. Thus, this template already contains one or more mutations. The oligonucleotide encoding the additional desired amino acid substitution(s) is then annealed to this template, and the resulting strand of DNA now encodes mutations from both the first and second rounds of mutagenesis. This resultant DNA can be used as a template in a third round of mutagenesis, and so on.

Eukaryotic expression systems may be utilized for secoisolariciresinol dehydrogenase production since they are capable of carrying out any required posttranslational modifications and of directing the enzyme to the proper membrane location. A representative eukaryotic expression system for this purpose uses the recombinant baculovirus, *Autographa californica* nuclear polyhedrosis virus (AcNPV; M. D. Summers and G. E. Smith, *A Manual of Methods for Boculovirus Vectors and Insect Cell Culture Procedures* (1986); Luckow et al., *Bio-technology* 6:47–55 (1987)) for expression of the secoisolariciresinol dehydrogenases of the invention. Infection of insect cells (such as cells of the species *Spodoptera frugiperda*) with the recombinant baculoviruses allows for the production of large amounts of the secoisolariciresinol dehydrogenase protein. In addition, the baculovirus system has other important advantages for the production of recombinant secoisolariciresinol dehydrogenase. For example, baculoviruses do not infect humans and can therefore be safely handled in large quantities. In the baculovirus system, a DNA construct is prepared including a DNA segment encoding secoisolariciresinol dehydrogenase and a vector. The vector may comprise the polyhedron gene promoter region of a baculovirus, the baculovirus flanking sequences necessary for proper cross-over during recombination (the flanking sequences comprise about 200–300 base pairs adjacent to the promoter sequence) and a bacterial origin of replication which permits the construct to replicate in bacteria. The vector is constructed so that (i) the DNA segment is placed adjacent (or operably-linked or "downstream" or "under the control of") to the polyhedron gene promoter and (ii) the promoter/secoisoiariciresinol dehydrogenase combination is flanked on both sides by 200–300 base pairs of baculovirus DNA (the flanking sequences).

To produce a secoisolariciresinol dehydrogenase DNA construct, a cDNA done encoding a full length secoisolariciresinol dehydrogenase is obtained using methods such as those described herein. The DNA construct is contacted in a host cell with baculovirus DNA of an appropriate baculovirus (that is, of the same species of baculovirus as the promoter encoded in the construct) under conditions such that recombination is effected. The resulting recombinant baculoviruses encode the full secoisolariciresinol dehydrogenase. For example, an insect host cell can be cotransfected or transfected separately with the DNA construct and a functional baculovirus. Resulting recombinant baculoviruses can then be isolated and used to infect cells to effect production of secoisolariciresinol dehydrogenase. Host insect cells include, for example, *Spodoptera frugiperda* cells. Insect host cells infected with a recombinant baculovirus of the present invention are then cultured under conditions allowing expression of the baculovirus-encoded secoisolariciresinol dehydrogenase. Recombinant protein thus produced is then extracted from the cells using methods known in the art.

Other eukaryotic microbes such as yeasts may also be used to practice this invention. The baker's yeast *Saccharomyces cerevisiae*, is a commonly used yeast, although several other strains are available. The plasmid YRp7 (Stinchcomb et al., *Nature* 282:39 (1979); Kingsman et al., *Gene* 7:141 (1979); Tschemper et al., *Gene* 10:157 (1980)) is commonly used as an expression vector in *Saccharomyces*. This plasmid contains the trp1 gene that provides a selection marker for a mutant strain of yeast lacking the ability to grow in tryptophan, such as strains ATCC No. 44,076 and PEP4-1 (Jones,*Genetics* 85:12 (1977)). The presence of the trp1 lesion as a characteristic of the yeast host cell genome then provides an effective environment for detecting transformation by growth in the absence of tryptophan. Yeast host cells are generally transformed using the polyethylene glycol method, as described by Hinnen (*Proc. Natl. Acad. Sci. USA* 75:1929 (1978)). Additional yeast transformation protocols are set forth in Gietz et al., *N.A.R* 20(17):1425 (1992); Reeves et al., *FEMS* 99:193–197 (1992).

Suitable promoting sequences in yeast vectors include the promoters for 3-phosphoglycerate kinase (Hitzeman et al., *J. Biol. Chem.* 255:2073 (1980)) or other glycolytic enzymes (Hess et al., *J. Adv. Enzyme Reg.* 7:149 (1968); Holland et al., *Biochemistry* 17:4900 (1978)), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In the construction of suitable expression plasmids, the termination sequences associated with these genes are also ligated into the expression vector 3' of the sequence desired to be expressed to provide polyadenylation of the mRNA and termination. Other promoters that have the additional advantage of transcription controlled by growth conditions are the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing yeast-compatible promoter, origin of replication and termination sequences is suitable.

Cell cultures derived from multicellular organisms, such as plants, may be used as hosts to practice this invention. Transgenic plants can be obtained, for example, by transferring plasmids that encode secoisolariciresinol dehydrogenase, and a selectable marker gene, e. g., the kan gene encoding resistance to kanamycin, into *Agrobacterium tumifaciens* containing a helper Ti plasmid as described in Hoeckema et al., *Nature* 303:179–181 (1983) and culturing the *Agrobacterium* cells with leaf slices of the plant to be transformed as described by An et al., *Plant Physiology* 81:301–305 (1986). Transformation of cultured plant host cells is normally accomplished through *Agrobacterium tumifaciens*, as described above. Cultures of mammalian host cells and other host cells that do not have rigid cell membrane barriers are usually transformed using the calcium phosphate method as originally described by Graham and Van der Eb (*Virology* 52:546 (1978)) and modified as described in Sections 16.32–16.37 of Sambrook et al., supra. However, other methods for introducing DNA into cells such as Polybrene (Kawai and Nishizawa, *Mol. Cell. Bio l.* 4:1172 (1984)), protoplast fusion (Schaffner, *Proc. Natl. Acad Sci. USA* 77:2163 (1980)), electroporation (Neumann et al., *EMBO J.* 1:841 (1982)), and direct microinjection into nuclei (Capecchi, *Cell* 22:479 (1980)) may also be used. Additionally, animal transformation strategies are reviewed in Monastersky G. M. and Robl, J. M., *Strategies in Trasgenic Animal Science*, ASM Press, Washington, D.C. (1995). Transformed plant calli may be selected through the selectable marker by growing the cells on a medium containing, e. g., kanamycin, and appropriate amounts of phytohormone such as naphthalene acetic acid and benzyladenine for callus and shoot induction. The plant cells may then be regenerated and the resulting plants transferred to soil using techniques well known to those skilled in the art.

In addition, a gene regulating secoisolarciresinol dehydrogenase production can be incorporated into the plant along with a necessary promoter which is inducible. In the practice of this embodiment of the invention, a promoter that only responds to a specific external or internal stimulus is fused to the target cDNA. Thus, the gene will not be transcribed except in response to the specific stimulus. As long as the gene is not being transcribed, its gene product is not produced.

An illustrative example of a responsive promoter system that can be used in the practice of this invention is the glutathione-S-transferase (GST) system in maize. GSTs are a family of enzymes that can detoxify a number of hydrophobic electrophilic compounds that often are used as pre-emergent herbicides (Weigand et al., *Plant Molecular Biology* 7:235–243 (1986)): Studies have shown that the GSTs are directly involved in causing this enhanced herbicide tolerance. This action is primarily mediated through a specific 1.1 kb mRNA transcription product. In short, maize has a naturally occurring quiescent gene already present that can respond to external stimuli and that can be induced to produce a gene product. This gene has previously been identified and cloned. Thus, in one embodiment of this invention, the promoter is removed from the GST responsive gene and attached to a secoisolariciresinol dehydrogenase gene that previously has had its native promoter removed. This engineered gene is the combination of a promoter that responds to an external chemical stimulus and a gene responsible for successful production of secoisolariciresinol dehydrogenase protein.

In addition to the methods described above, several methods are known in the art for transferring cloned DNA into a wide variety of plant species, including gymnosperms, angiosperms, monocots and dicots (see, e. g., Glick and Thompson, eds., *Methods in Plant Molecular Biology*, CRC Press, Boca Raton, Fla. (1993)). Representative examples include electroporation-facilitated DNA uptake by protoplasts (Rhodes et al., *Science* 240(4849):204–207 (1988)); treatment of protoplasts with polyethylene glycol (Lyznik et al., *Plant Molecular Biology* 13:151–161 (1989)); and bombardment of cells with DNA laden microprojectiles (Klein et al., *Plant Physiol.* 91:440–444 (1989) and Boynton et al., *Science* 240(4858):1534–1538 (1988)). Numerous methods now exist, for example, for the transformation of cereal crops (see, e. g., McKinnon, G. E. and Henry, R. J., *J. Cereal Science*, 22(3):203–210 (1995); Mendel, R. R. and Teeri, T. H., *Plant and Microbial Biotechnology Research Series*, 3:81–98, Cambridge University Press (1995); McElroy, D. and Brettell, R. I. S., *Trends in Biotechnology*, 12(2):62–68 (1994); Christou et al., *Trends in Biotechnology*, 10(7) :239–246 (1992); Christou, P. and Ford, T. L., *Annals of Botany*, 75(5): 449–454 (1995); Park et al., *Plant Molecular Biology*, 32(6):1135–1148 (1996); Altpeter et al., *Plant Cell Reports*, 16:12–17 (1996)). Additionally, plant transformation strategies and techniques are reviewed in Birch, R. G., *Ann Rev Plant Phys Plant Mol Biol* 48:297 (1997); Forester et al., *Exp. Agric.* 33:15–33 (1997). Minor variations make these technologies applicable to a broad range of plant species. Each of the foregoing publications disclosing methods for genetically transforming plants are incorporated herein by reference.

By way of non-limiting example, in the practice of the present invention the following plant genuses and species can be genetically transformed with a nucleic acid molecule encoding a secoisolariciresinol dehydrogenase protein, and/or a nucleic acid molecule that is complementary to at least a portion of a nucleic acid molecule encoding a secoisolariciresinol dehydrogenase protein: Arachis (including peanut); Arecacum (including oil palms); Brassica (including arugula, bok choi, brocolli, brussel sprouts, cabbage, cauliflower, kale, mustard, radishes, rape, turnip, raddichio); Carthamus (including safflower); Cocos, (including coconut); Gossypium (including cotton); Glycine (including soybeans); Helianthus (including sunflower, Jerusalem artichoke); Linum (including flax); Sesamum (including sesame); Agaricus (including table mushrooms); Amoracia (including horseradish); Allium (including chives, garlic, leek, onion); Apicum (including celery); Asparagus (including asparagus); Beta (including beets, sugar beets); Camellia (including tea); Capsicum (including bell, chile and other peppers); Chenopodacum (including swiss chard, spinach); Cicer (including chick peas, garbanzos); Chicorum (including endive); Coffea (including coffee); Convolvutacum (including sweet potato); Coriandrum (including coriander, cilantro); Cynara (including artichoke); Daucus (including carrots); Discorum (including yams); Hibiscus (including okra); Lactuca (including bibb, boston, iceberg, leaf and other lettuces); Lens (including lentils); Pastinaca (including parsnip); Phaseolus (including field, kidney, navy, pinto, wax beans); Pisum (including peas, snow peas, sugar snap peas); Rheum (including rhubarb); Solanum (including eggplant and potatoes); Vigna (including adzuki bean, blackeyed peas, mung beans); Carya (including pecan); Corylus (including hazelnut); Cucumis (including cucumber, melon); Cucurbita (including pumpkin, squash, zucchini); Juglans (including walnut); Olea, (including olives); Prunus, (including almonds); Pistacia (including pistachio); Zea; Sorghum; Hordeum; Elusine; Panicum; Paspalum; Pennisetum; Setera; Avena; Oryza; Secale; Triticum; Aclinidia (including Kiwi); Carica (includes papaya); Citrus (including grapefruit, lemon, orange, tangerine); Fragaria (including strawberries); Lycopersicom (including tomato); Malus (including apples); Mangifera (including mango); Musa (including bananas); Prunus (including apricots, cherries, nectarines, peaches, plums); Pyrus (including pears, Asian pears); Ribes (including currants, gooseberries); Rubus (including blackberry, raspberry); Vaccinium (including blueberries, cranberries, lingonberries); Vitis (including grapes).

Each of the foregoing plant transformation techniques has advantages and disadvantages. In each of the techniques, DNA from a plasmid is genetically engineered such that it contains not only the gene of interest, but also selectable and screenable marker genes. A selectable marker gene is used to select only those cells that have integrated copies of the plasmid (the construction is such that the gene of interest and the selectable and screenable genes are transferred as a unit). The screenable gene provides another check for the successful culturing of only those cells carrying the genes of interest. A commonly used selectable marker gene is neomycin phosphotransferase II (NPT II). This gene conveys resistance to kanamycin, a compound that can be added directly to the growth media on which the cells grow. Plant cells are normally susceptible to kanamycin and, as a result, die. The presence of the NPT II gene overcomes the effects of the kanamycin and each cell with this gene remains viable. Another selectable marker gene which can be employed in the practice of this invention is the gene which confers resistance to the herbicide glufosinate (Basta). A screenable gene commonly used is the β-glucuronidase gene (GUS). The presence of this gene is characterized using a histochemical reaction in which a sample of putatively transformed cells is treated with a GUS assay solution. After an appropriate incubation, the cells containing the GUS gene turn blue. Preferably, the plasmid will contain both selectable and screenable marker genes.

The plasmid containing one or more of these genes is introduced into either plant protoplasts or callus cells by any of the previously mentioned techniques. If the marker gene is a selectable gene, only those cells that have incorporated the DNA package survive under selection with the appropriate phytotoxic agent. Once the appropriate cells are identified and propagated, plants are regenerated. Progeny from the transformed plants must be tested to insure that the DNA package has been successfully integrated into the plant genome.

Mammalian host cells may also be used in the practice of the invention. Examples of suitable mammalian cell lines include monkey kidney CVI line transformed by SV40 (COS-7, ATCC CRL 1651); human embryonic kidney line 293S (Graham et al., *J. Gen. Virol.* 36:59 (1977)); baby hamster kidney cells (BHK, ATCC CCL 10); Chinese hamster ovary cells (Urlab and Chasin, *Proc. Natl. Acad. Sci USA* 77:4216 (1980)); mouse sertoli cells (TM4, Mather, *Biol. Reprod.* 23:243 (1980)); monkey kidney cells (CVI-76, ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor cells (MMT 060562, ATCC CCL 51); rat hepatoma cells (HTC, MI.54, Baumann et al., *J. Cell Biol.* 85:1 (1980)); and TRI cells (Mather et al., *Annals N.Y. Acad. Sci.* 383:44 (1982)). Expression vectors for these cells ordinarily include (if necessary) DNA sequences for an origin of replication, a promoter located in front of the gene to be expressed, a ribosome binding site, an RNA splice site, a polyadenylation site, and a transcription terminator site.

Promoters used in mammalian expression vectors are often of viral origin. These viral promoters are commonly derived from polyoma virus, Adenovirus 2, and most frequently Simian Virus 40 (SV40). The SV40 virus contains two promoters that are termed the early and late promoters. These promoters are particularly useful because they are both easily obtained from the virus as one DNA fragment that also contains the viral origin of replication (Fiers et al., *Nature* 273:113 (1978)). Smaller or larger SV40 DNA fragments may also be used, provided they contain the approximately 250-bp sequence extending from the HindIII site toward the BgII site located in the viral origin of replication.

Alternatively, promoters that are naturally associated with the foreign gene (homologous promoters) may be used provided that they are compatible with the host cell line selected for transformation.

An origin of replication may be obtained from an exogenous source, such as SV40 or other virus (e. g., Polyoma, Adeno, VSV, BPV) and inserted into the cloning vector. Alternatively, the origin of replication may be provided by the host cell chromosomal replication mechanism. If the vector containing the foreign gene is integrated into the host cell chromosome, the latter is often sufficient.

The use of a secondary DNA coding sequence can enhance production levels of secoisolariciresinol dehydrogenase protein in transformed cell lines. The secondary coding sequence typically comprises the enzyme dihydrofolate reductase (DHFR). The wild-type form of DHFR is normally inhibited by the chemical methotrexate (MTX). The level of DHFR expression in a cell will vary depending on the amount of MTX added to the cultured host cells. An additional feature of DHFR that makes it particularly useful as a secondary sequence is that it can be used as a selection marker to identify transformed cells. Two forms of DHFR are available for use as secondary sequences, wild-type DHFR and MTX-resistant DHFR. The type of DHFR used in a particular host cell depends on whether the host cell is DHFR deficient (such that it either produces very low levels of DHFR endogenously, or it does not produce functional DHFR at all). DHFR-deficient cell lines such as the CHO cell line described by Urlaub and Chasin, supra, are transformed with wild-type DHFR coding sequences. After transformation, these DHFR-deficient cell lines express functional DHFR and are capable of growing in a culture medium lacking the nutrients hypoxanthine, glycine and thymidine. Nontransformed cells will not survive in this medium.

The MTX-resistant form of DHFR can be used as a means of selecting for transformed host cells in those host cells that endogenously produce normal amounts of functional DHFR that is MTX sensitive. The CHO-K1 cell line (ATCC No. CL 61) possesses these characteristics, and is thus a useful cell line for this purpose. The addition of MTX to the cell culture medium will permit only those cells transformed with the DNA encoding the MTX-resistant DHFR to grow. The nontransformed cells will be unable to survive in this medium.

Prokaryotes may also be used as host cells for the initial cloning steps of this invention. They are particularly useful for rapid production of large amounts of DNA, for production of single-stranded DNA templates used for site-directed mutagenesis, for screening many mutants simultaneously, and for DNA sequencing of the mutants generated. Suitable prokaryotic host cells include *E. coli* K12 strain 294 (ATCC No. 31,446), *E. coli* strain W3110 (ATCC No. 27,325) *E. coli* X1776 (ATCC No. 31,537), and *E. coli* B; however many other strains of *E. coli*, such as HB101, JM101, NM522, NM538, NM539, and many other species and genera of prokaryotes including bacilli such as *Bacillus subtilis*, other enterobacteriaceae such as *Salmonella typhimurium* or *Serratia marcesans*, and various Pseudomonas species may all be used as hosts. Prokaryotic host cells or other host cells with rigid cell walls are preferably transformed using the calcium chloride method as described in section 1.82 of Sambrook et al., supra. Alternatively, electroporation may be used for transformation of these cells. Prokaryote transformation techniques are set forth in Dower, W. J., in *Genetic Engineering, Principles and Methods*, 12:275–296, Plenum Publishing Corp. (1990); Hanahan et al., *Meth. Enzymol.*, 204:63 (1991).

As a representative example, cDNA sequences encoding secoisolariciresinol dehydrogenase may be transferred to the $(His)_6$.Tag pET vector commercially available (from Novagen) for overexpression in *E. coli* as heterologous host. This pET expression plasmid has several advantages in high level heterologous expression systems. The desired cDNA insert is ligated in frame to plasmid vector sequences encoding six histidines followed by a highly specific protease recognition site (thrombin) that are joined to the amino terminus codon of the target protein. The histidine "block" of the expressed fusion protein promotes very tight binding to immobilized metal ions and permits rapid purification of the recombinant protein by immobilized metal ion affinity chromatography. The histidine leader sequence is then cleaved at the specific proteolysis site by treatment of the purified protein with thrombin, and the secoisolariciresinol dehydrogenase protein eluted. This overexpression-purification system has high capacity, excellent resolving power and is fast, and the chance of a contaminating *E. coli* protein exhibiting similar binding behavior (before and after thrombin proteolysis) is extremely small.

As will be apparent to those skilled in the art, any plasmid vectors containing replicon and control sequences that are derived from species compatible with the host cell may also be used in the practice of the invention. The vector usually has a replication site, marker genes that provide phenotypic selection in transformed cells, one or more promoters, and a polylinker region containing several restriction sites for insertion of foreign DNA. Plasmids typically used for transformation of *E. coli* include pBR322, pUC18, pUC19, pUCl18, pUC119, and Bluescript M13, all of which are described in Sections 1.12–1.20 of Sambrook et al., supra. However, many other suitable vectors are available as well. These vectors contain genes coding for ampicillin and/or tetracycline resistance which enables cells transformed with these vectors to grow in the presence of these antibiotics.

The promoters most commonly used in prokaryotic vectors include the β-lactamase (penicilinase) and lactose promoter systems (Chang et al. *Nature* 375:615 (1978); Itakura et al., *Science* 198:1056 (1977); Goeddel et al., *Nature* 281:544 (1979)) and a tryptophan (trp) promoter system (Goeddel et al., *Nucl. Acids Res.* 8:4057 (1980); EPO Appl. Publ. No. 36,776), and the alkaline phosphatase systems. While these are the most commonly used, other microbial promoters have been utilized, and details concerning their nucleotide sequences have been published, enabling a skilled worker to ligate them functionally into plasmid vectors (see Siebenlist et al., *Cell* 20:269 (1980)).

Many eukaryotic proteins normally secreted from the cell contain an endogenous secretion signal sequence as part of the amino acid sequence. Thus, proteins normally found in the cytoplasm can be targeted for secretion by linking a signal sequence to the protein. This is readily accomplished by ligating DNA encoding a signal sequence to the 5' end of the DNA encoding the protein and then expressing this fusion protein in an appropriate host cell. The DNA encoding the signal sequence may be obtained as a restriction fragment from any gene encoding a protein with a signal sequence. Thus, prokaryotic, yeast, and eukaryotic signal sequences may be used herein, depending on the type of host cell utilized to practice the invention. The DNA and amino acid sequence encoding the signal sequence portion of several eukaryotic genes including, for example, human growth hormone, proinsulin, and proalburin are known (see Stryer, *Biochemistry* W. H. Freeman and Company, New York, N.Y., p. 769 (1988)), and can be used as signal sequences in appropriate eukaryotic host cells. Yeast signal sequences, as for example acid phosphatase (Arima et al., *Nucleic Acids Res.* 11:1657 (1983)), alpha-factor, alkaline phosphatase and invertase may be used to direct secretion from yeast host cells. Prokaryotic signal sequences from genes encoding, for example, LamB or OmpF (Wong et al.,*Gene* 68:193 (1988)), MalE, PhoA, or beta-lactamase, as well as other genes, may be used to target proteins from prokaryotic cells into the culture medium.

Trafficking sequences from plants, animals and microbes can be employed in the practice of the invention to direct the gene product to the cytoplasm, endoplasmic reticulum, mitochondria or other cellular components, or to target the protein for export to the medium. These considerations apply to the overexpression of secoisolariciresinol dehydrogenase, and to direction of expression within cells or intact organisms to permit gene product function in any desired location.

The construction of suitable vectors containing DNA encoding replication sequences, regulatory sequences, phenotypic selection genes and the secoisolariciresinol dehydrogenase DNA of interest are prepared using standard recombinant DNA procedures. Isolated plasmids and DNA fragments are cleaved, tailored, and ligated together in a specific order to generate the desired vectors, as is well known in the art (see, for example, Sambrook et al., supra).

As discussed above, secoisolariciresinol dehydrogenase variants, are preferably produced by means of mutation(s) that are generated using the method of site-specific mutagenesis. This method requires the synthesis and use of specific oligonucleotides that encode both the sequence of the desired mutation and a sufficient number of adjacent nucleotides to allow the oligonucleotide to stably hybridize to the DNA template.

A secoisolariciresinol dehydrogenase gene, or an antisense nucleic acid fragment complementary to all or part of a secoisolariciresinol dehydrogenase gene, may be introduced, as appropriate, into any plant species for a variety of purposes including, but not limited to: altering or improving the color, texture, durability and pest-resistance of wood tissue, especially heartwood tissue; reducing the formation, or otherwise altering the levels, of lignans and/or lignins in plant species, such as corn, which are useful as animal fodder, thereby enhancing the availability of the cellulose fraction of the plant material to the digestive system of animals ingesting the plant material; reducing, or otherwise altering the levels of, the lignan/lignin content of plant species utilized in pulp and paper production, thereby making pulp and paper production easier and cheaper; improving the defensive capability of a plant against predators and pathogens by enhancing the production of defensive lignans or lignins; the alteration of other ecological interactions mediated by lignans or lignins; producing elevated levels of optically-pure lignan enantiomers as medicines or food additives; introducing, enhancing or inhibiting the production of secoisolariciresinol dehydrogenases, or the production of matairesinol and its derivatives. A secoisolariciresinol dehydrogenase gene may be introduced into any organism for a variety of purposes including, but not limited to: introducing, enhancing or inhibiting the production of secoisolariciresinol dehydrogenase, or the production of matairesinol and its derivatives. Any art-recognized technique, utilizing a nucleic acid molecule of the present invention, can be used to enhance, inhibit or otherwise alter the production of secoisolariciresinol dehydrogenase, or the production of matairesinol and its derivatives.

The foregoing may be more fully understood in connection with the following representative examples, in which "Plasmids" are designated by a lower case p followed by an alphanumeric designation. The starting plasmids used in this invention are either commercially available, publicly available on an unrestricted basis, or can be constructed from such available plasmids using published procedures. In addition, other equivalent plasmids are known in the art and will be apparent to the ordinary artisan.

"Digestion", "cutting" or "cleaving" of DNA refers to catalytic cleavage of the DNA with an enzyme that acts only at particular locations in the DNA. These enzymes are called restriction endonucleases, and the site along the DNA sequence where each enzyme cleaves is called a restriction site. The restriction enzymes used in this invention are commercially available and are used according to the instructions supplied by the manufacturers. (See also Sections 1.60–1.61 and Sections 3.38–3.39 of Sambrook et al., supra.)

"Recovery" or "isolation" of a given fragment of DNA from a restriction digest means separation of the resulting DNA fragment on a polyacrylamide or an agarose gel by electrophoresis, identification of the fragment of interest by comparison of its mobility versus that of marker DNA fragments of known molecular weight, removal of the gel section containing the desired fragment, and separation of the gel from DNA. This procedure is known generally. For example, see Lawn et al. (*Nucleic Acids Res.* 9:6103–6114 (1982)), and Goeddel et al. (*Nucleic Acids Res.*, supra), The following examples merely illustrate the best mode now contemplated for practicing the invention, but should not be construed to limit the invention.

EXAMPLE 1

Isolation of Secoisolariciresinol Dehydrogenase Protein from *Forsythia intermedia*

The following materials and methods were utilized in Examples 1 and 2, unless otherwise stated.

Plant materials

*F. intermedia* plants were either obtained from Bailey's Nursery (var. Lynwood Gold, St. Paul, Minn.), and maintained in Washington State University greenhouse facilities, or were gifts from the local community.

Materials

All solvents and chemicals used were reagent or HPLC grade. DEAE cellulose and Adenosine 2',5' -diphosphate-Sepharose were purchased from Sigma; MonoP HR-5/20 and SDS-PAGE molecular weight standards were obtained from Pharmacia LKB Biotechnology, Inc. Taq thermostable DNA polymerase and restriction enzymes (BamH I, Nde I, Spe I) were obtained from Promega. pT7Blue T-vector and competent NovaBlue cells were purchased from Novagen and radiolabeled nucleotide ([$\alpha$-$^{32}$P]dCTP) was from DuPont NEN. Oligonucleotide primers for polymerase chain reaction (PCR) and sequencing were synthesized by Gibco BRL Life Technologies.

Instrumentation $^1$H and $^{13}$C nuclear magnetic resonance spectra were recorded on a Bruker AMX300 using CDCl$_3$ as solvent with chemical shifts ($\delta$ ppm) reported downfield from tetramethylsilane (internal standard). High performance liquid chromatography was carried out using either reversed phase (Waters, Nova-pak C$_{18}$, 150×3.9 mm inner diameter) or chiral (Daicel, Chiralcel OD, 250×4.6 mm inner diameter) columns with detection at 280 nm. Radioactive samples were analyzed in ScintiVerse II (Fisher Scientific) and measured using a liquid scintillation counter (Packard, Tricarb 2000 CA). Mass spectra (EI mode) were obtained using a Waters Integrity™ System equipped with a Thermabeam™ Mass Detector. Amino acid sequences were obtained using an Applied Biosystems protein sequencer with on-line HPLC detection, according to the manufacturer's instructions. UV (including RNA and DNA determinations at 260 nm) spectra were recorded on a Lambda 6 UV/VIS spectrophotometer. A Temptronic II thermocycler (Thernolyne) was used for all PCR amplifications. Purification of plasmid DNA for sequencing employed a Wizard Plus SV Miniprep DNA Purification System (Promega), with DNA sequences determined using an Applied Biosystems Model 373A automated sequencer.

Synthesis of (±)-[9,9'-$^3$H$_2$]Secoisolariciresinols

To [9-$^3$H$_2$]coniferyl alcohol (0.5 mM in acetone, 65 MBq, 7 ml) was added FeCl$_3$ (aqueous solution, 700 mg, 24 ml), at room temperature. Following stirring for 10 min, the reaction mixture was extracted with ether (30 ml ×3). The ether solubles were combined, extracted with water (20 ml), dried with Na$_2$SO$_4$, and evaporated to dryness in vacuo. The residue was reconstituted in a minimum amount of CH$_2$Cl$_2$ and applied to a silica gel column (15×2.5 cm inner diameter) eluted with CH$_2$Cl$_2$:ether (4:1) to give pure (±)-[9,9'-$^3$H$_2$]pinoresinol (0.1 mM, 13 MBq, 36 mg, 20%). To a stirred solution of (±)-[9.9'-$^3$H$_2$]pinoresinols (0.1 mM in MeOH, 13 MBq, 5 ml) was added Pd/C (10%, 80 mg) under H$_2$. After 24 h reduction, the catalyst was removed by filtration, washed with MeOH (5 ml); the MeOH solubles were combined and evaporated to dryness in vacuo to afford, following preparative silica TLC (developed with EtOAc:hexanes:methanol 10:10:1), (±)-[9,9'-$^3$H$_2$] secoisolariciresinols (0.07 mM, 9.1 MBq, 25 mg, 70%).

Synthesis of (±)-[Ar-$^2$H]secoisolariciresinol

[Ar-$^2$H]secoisolariciresinol was synthesized as described in Umezawa, T., Davin, L. B. and Lewis, N. G., *J. Biol. Chem.*, 266: 10210–10217(1991).

Enzyme Assays (1) Radiochemical Assays with (±)-[9,9'-$^3$H$_2$] secoisolariciresinols Secoisolariciresinol dehydrogenase activity was assayed by monitoring the formation of (−)-[9'-$^3$H$_2$]matairesinol. Each assay consisted of NAD (50 mM in 0.1 M potassium phosphate buffer, pH 7, 5 µl), (±)-[9,9'-$^3$H$_2$] secoisolariciresinols (28 nM, 130 MBq/mmol in ethanol, 5 µl) and buffer (50 mM Tris-HCl, pH 8.8, 470 µl ). The enzymatic reaction was initiated by addition of the enzyme preparation (20 µl). After 1 h incubation at 30° C. with shaking, the mixture was extracted with EtOAc (500 µl x2) containing unlabelled (±)-matairesinols (200 µg) as radiochemical carriers. After centrifugation (13,800×g, 5 min) the EtOAc solubles were removed, evaporated to dryness in vacuo, reconstituted in MeOH:3% acetic acid in H$_2$O (1:1, 200 µl), and an aliquot (20 µl) subjected to reversed-phase column chromatography. The elution conditions were as follows: linear gradient acetonitrile/3% acetic acid in H$_2$O from 10:90 to 30:70 between 0 and 35 min; then to 5:95 in 5 min and finally isocratic at 5:95 for 5 min, at a flow rate of 1 ml min$^{-1}$, and detection at 280 nm. Fractions corresponding to matairesinol were individually collected, aliquots removed for liquid scintillation counting, and the remainder freeze-dried.

(2) Assays with (±)-[Ar-$^2$H]secoisolariciresinol

Two mg [Ar-$^2$H]secoisolariciresinol in 500 µl EtoH was added into 10 mL 50 mM pH 8.8 Tris-HCl buffer, which had ca. 2 µg dehydrogenase and 40 µmol NAD. After 1 hr incubation at 30° C. with shaking, the mixture was extracted with EtOAc (10 ml x2). The solvent was evaporated and the extract was purified by HPLC. The matairesinol peak was collected, freeze-dried, and gave 0.8 mg matairesinol when analyzed by MS.

Chemical Conversion of Enzymatically Formed [9'-$^3$H$_2$] Matairesinol to [9'-$^3$H$_2$]Secoisolariciresinol

[9'-$^3$H$_2$]Matairesinol (0.5 kBq), collected after reversed-phase column chromatography, was reduced with LiAlH$_4$ to give [9'-$^3$H$_2$]secoisolariciresinol (0.26 kBq). Chiral HPLC (Daicel OD) analysis revealed that only (−)-[9-$^3$H] secoisolariciresinol was formed, indicating that only (−)-[9-$^3$H]matairesinol had been enzymatically generated.

Synthesis of Lactol

To matairesinol (in toluene, 0.5 mM, 2 ml) was added diisobutylaluminium hydride (in hexanes, 1 M, 0.6 ml) dropwise at −78° C. The reaction mixture was stirred for one hour at −78° C., quenched with a few drops of HCl (2 N), then extracted with EtOAc (20 ml). The EtOAc solubles were extracted with water (6 ml), evaporated to dryness in vacuo and subjected to preparative TLC (developed with EtOAc:hexanes:methanol 10:10:1) to afford the required lactol (0.35 mM, 70%).

Secoisolariciresinol dehydrogenase protein was isolated from *Forsythia intermedia*, and partially sequenced, in the following manner.

General Procedures for the Enzyme Purification

All manipulations were carried out at 4° C. with chromatographic eluents monitored at 280 nm, unless otherwise indicated. Protein concentrations, using γ-globulin as standard, were determined by the method of Bradford (Bradford, M. M., *Analyt. Biochem.*, 117: 248 (1976)).

Polyacrylamide gel electrophoresis was performed with Laemmli's buffer system under denaturing or non-denaturing conditions and gradient gels (4–15%, BioRad) (Laemmli, U. K., *Nature*, 227, 680 (1970)); proteins were then visualized by silver staining (Morrissey, J. H., *Anal. Biochem.*, 117, 307(1981)).

Preparation of Cell-free Extracts

*F. intermedia* stems (2 kg) were frozen (liquid N$_2$) and pulverized in a Waring Blender (Model CB6). The resulting powder was homogenized with Tris-HCl buffer (50 mM, pH 7.5, 2 L) containing 5 mM dithiothreitol (buffer A). The homogenate was filtered through four layers of cheesecloth into a beaker containing polyvinylpolypyrrolidone (10% w/v). The filtrate was centrifuged (10,000×g, 15 min) and the resulting supernatant fractionated with (NH$_4$)$_2$SO$_4$. Proteins precipitating between 30–60% saturation were recovered by centrifugation (10,000×g, 30 min) with the pellet then reconstituted in a minimum amount of buffer A.

DEAE Chromatography

The crude enzyme preparation (445 mg in 90 ml buffer A, 4.1 nmol h$^{-1}$ mg$^{-1}$) was applied to a DEAE cellulose column (40×2.6 cm inner diameter) equilibrated in buffer A. Secoisolariciresinol dehydrogenase was eluted (after washing the column with 25 ml of buffer A) with a linear NaCl gradient (0–2 M in 500 ml) in buffer A at a flow rate of 2.5 ml min$^{-1}$. Active fractions were combined, concentrated by ultrafiltration (Amicon, YM10 membrane) to 50 ml and dialyzed (25 mM Tris-HCl buffer, pH 7.5) overnight.

Affinity (2',5'-ADP-Sepharose) Chromatography

The active fractions from the DEAE cellulose chromatography (201 mg, 14.4 nmol h$^{-1}$ mg$^{-1}$) were applied to a 2',5'-ADP-Sepharose (10×1 cm inner diameter) column previously equilibrated in Tris-HCl buffer (25 mM, pH 7.5). The column was first washed with 20 ml of the same buffer, then with 50 ml Buffer A containing 500 mM NaCl at a flow rate of 1 ml min$^{-1}$ and finally secoisolariciresinol dehydrogenase was eluted with NAD (10 mM) in buffer A. The active fractions were combined and dialyzed 16 hours against buffer A.

MonoP (HR 5/20) Column Chromatography

Active protein (185 µg, 8405 nmol h$^{-1}$ mg$^{-1}$) from the preceding step was applied to a MonoP column equilibrated in buffer A, washed with buffer A (8 ml) and eluted with a linear NaCl gradient (0–2 M in 145 ml) in buffer A at a flow rate of 1 ml min$^{-1}$. The active fractions (74 µg, 17.7 µmol h$^{-1}$ mg$^{-1}$) were combined, dialyzed against buffer A, then rechromatographed on the MonoP column using the procedure described above. Secoisolariciresinol dehydrogenase (31 µg, 24.27 µmol h$^{-1}$ mg$^{-1}$) obtained was next analyzed by SDS-PAGE.

Amino Acid Sequencing (−)-Secoisolariciresinol dehydrogenase was first submitted to SDS-polyacrylamide gel electrophoresis and then electroblotted onto a PVDF membrane using the procedures described by Hunkapiller et al. (Hunkapiller, M., *Methods Enzymol.*, 91:227) and Matsudaira (Matsudaira, P., *J. Biol. Chem.*, 262:10035 (1987)), respectively. Briefly, a minigel was first electrophoresed in running buffer (25 mM Tris, 192 mM glycine and 0.1% SDS) containing reduced glutathione (5 µM) for 30 min at 8 mA constant current after which the cathode buffer was replaced with fresh running buffer containing 0.1 M thioglycolate.

To (−)-secoisolariciresinol dehydrogenase was added loading buffer, with the mixture next heated at 55° C. for 15 min, loaded onto the minigel and then electrophoresed at 20 mA constant current for 45 min. After electrophoresis, the gel was soaked in transfer buffer (10 mM CAPS, 10% methanol, pH 11.0) for 10 min, then placed into a blotting apparatus and electroeluted for 1 hour at 150 mA constant current in transfer buffer at 4° C. After staining with Coomassie blue R-250, the band corresponding to (−)-secoisolariciresinol dehydrogenase was cut, rinsed with deionized H$_2$O and directly submitted to amino acid sequencing to obtain the N-terminal sequence (SEQ ID NO:11).

Trypsin digestion

To the pure (−)-secoisolariciresinol dehydrogenase (200 pmol in 60 μl water), was added urea to give a final concentration of 8 M. After incubation at 37° C. for 30 min, 0.2 M ammonium bicarbonate/1 mM CaCl$_2$ (60 μl) and trypsin (0.5 μg/μl in 0.01% TFA, 2 μl) were added, and the mixture digested at 37° C. for 12 h after which more trypsin (2 μl) was added, with the digestion allowed to continue for another 12 h. The enzymatic reaction was stopped by addition of TFA (4 μl). The resulting mixture, subjected to reversed-phase HPLC analysis (C-8 column, Applied Biosystems), was eluted with a linear gradient from 0 to 100% acetonitrile (in 0.1% TFA) in 2 hours at a flow rate of 0.2 ml min$^{-1}$ with detection at 214 nm. Fractions containing individual oligopeptide peaks were collected manually, concentrated (SpeedVac) and submitted to amino acid sequencing as before. The amino acid sequence of two secoisolariciresinol dehydrogenase trypsin-liberated oligopeptides are set forth in SEQ ID NO:12 (peptide 1) and SEQ ID NO:13 (peptide 2).

EXAMPLE 2

Cloning of Secoisolariciresinol Dehydrogenase cDNAs from Forsythia intermedia

F. intermedia Stem cDNA Library Synthesis

Total RNA (approximately 300 μg g$^{-1}$ fresh weight) was obtained (Dong, J. Z. and Dunstan, D. I., Plant Cell Reports 15:516–521(1996)) from young green stems of greenhouse grown F. intermedia plants (var. Lynwood Gold). An F. intermedia stem cDNA library was constructed using 5 μg of purified poly A+ mRNA (Oligotex-dt(Suspension, QIAGEN) with the ZAP-cDNAII Gold packaging extract (Stratagene), with a titer of 1.2 ×10$^6$ pfu for the primary library. A 30 ml portion of the amplified library (1.2×10$^{10}$ pfu/ml; 158 ml total) (Sambrook, J., Fritsch, E. F. and Maniatis, T. (1989) Molecular Cloning, Edition 2, Cold Spring Harbor Laboratory Press, Cold Spring Harbor) was used to obtain pure cDNA library DNA for PCR (Ausubel, F. M., Brent, R., Kingston, R. E., Moore, D. D., Seidman, J. G., Smith, J. A. and Struhl, K. (1991) Current Protocols in Molecular Biology. 2 vols., Greene Publishing Associates and Wiley Interscience, John Wiley & Sons, New York, N.Y.).

(−)-Secoisolariciresinol Dehydrogenase DNA Probe Synthesis

The N-terminal (SEQ ID NO:11) and internal peptide amino acid sequences (SEQ ID NO:12 and SEQ ID NO:13) were used to construct degenerate oligonucleotide primers. Primer DEHYF26 (SEQ ID NO:14) was constructed based on the amino acid sequence of peptide 1 having the amino acid sequence set forth in SEQ ID NO:12. Primers DEHYF30RevA (SEQ ID NO:15) and DEHYF30RevB (SEQ ID NO:16) were each constructed based on the amino acid sequence of peptide 2 having the amino acid sequence set forth in SEQ ID NO:13. Purified F. intermedia cDNA library DNA (2 ng) was used as the template in 100 μl PCR reactions (10 mM Tris-HCl [pH 9.0], 50 mM KCl, 0.1% Triton X100, 2.5 mM MgCl$_2$, 0.2 mM each dNTP and 2.5 units Taq DNA polymerase) with primer DEHYF26 (SEQ ID NO:14) and either primer DEHYF30RevA (SEQ ID NO:15) or primer DEHY30RevB (SEQ ID NO:16). PCR amplification was carried out in a thermocycler with 35 cycles of 94° C. denaturing for 1 min, 50° C. annealing for 2 min, and 72° C. extension for 3 min. PCR products were resolved in 1.5% agarose gels where a single band of approximately 200 bp was obtained. The resulting PCR product was then ligated into pT7Blue T-vector and transformed into competent NovaBlue cells according to Novagen's instructions. The recombinant plasmid was used for DNA sequencing. DNA sequence analysis revealed that the insert coded for one of the initial internal trypsin digest fragments obtained from the native plant protein. A BamH I/Spe I fragment of approximately 200 bp was cut from the plasmid preparation and used as a probe to screen the cDNA library.

Library screening

Approximately 300,000 pfu of F. intermedia amplified cDNA library were plated for screening, according to Stratagene's instructions. Plaques were blotted onto Magna Nylon membrane circles (Micron Separations Inc.), which were then allowed to air dry. The membranes were placed between two layers of Whatman 3 MM Chromatography paper. cDNA library phage were fixed to the membranes and denatured in one step by autoclaving for 2 min at 100° C. with fast exhaust. The membranes were washed for 30 min at 37° C. in 2×SSC and prehybridized for 12 h with gentle shaking at 45° C. in a hybridization solution consisting of 6×SSC, 0.5% SDS, and 5×Denhardt's reagent. The [$^{32}$P] radiolabeled 200 bp probe was denatured by boiling for 10 min, quickly cooled on ice for 10 min, and added to the prehybridized membranes in 30 ml of fresh hybridization solution. Hybridization was performed at 45° C. for 24 h with gentle shaking. Membranes were then washed in 4×SSC at room temperature for 10 min, followed by an additional wash in 4×SSC at 45° C. for 10 min. Membranes were exposed to X-ray film (Jersey Lab Supply) with intensifying screens at −80° C. for 24 h.

One positive signal was obtained from this screening which, after three rounds of screening, was in vivo excised and grown for a plasmid prep to use for sequencing. A BLAST search comparison showed that the protein encoded for by this gene had a similarity of 76% to an alcohol dehydrogenase from Solanum lycopersicum (Jacobsen, S. E. and Olszewski, N. E., Planta, 198:78(1996)). However, the clone was truncated at the N-terminal end by approximately 60 amino acid residues, as was indicated by comparison to the original N-terminal sequence analysis of (−)-secoisolariciresinol dehydrogenase. Additional screenings of the Forsythia cDNA library using similar hybridization conditions were performed with probes obtained from restriction enzyme digested fragments of the truncated clone. These probes yielded only one additional clone which had the same sequence and the same truncation as the original clone.

An alternative scheme was used to obtain the complete clone from the original cDNA library stock. A primer, DEHY19REV (SEQ ID NO:17), was made from the 3' end of the truncated clone and used with the T3 primer in a PCR with the original Forsythia cDNA library purified phage DNA as template, but failed to yield cDNA clones having the complete N-terminus. Consequently, another primer, DEHYF30REVB (SEQ ID NO:18), was synthesized from the 3' end of the truncated clone and used with the T3 primer (SEQ ID NO:19) in a PCR with the original Forsythia cDNA library purified phage DNA as template. This PCR product, when cloned into TA vector, resulted in a clone having the complete N-terminus (SEQ ID NO:11) which was obtained from the initial amino acid sequencing of the blotted protein, A new primer, DEHYNTERM1 (SEQ ID NO:20), made from the N-terminal DNA sequence of this clone was used with the T7 primer (SEQ ID NO:21) and again with the original purified *Forsythia* cDNA library as template. The resulting PCR band of 1 kb was purified on an agarose gel, eluted by using a Microcon 30 (AMICON) and cloned directly into a TA vector (Invitrogen). This provided a clone (DEHY130) (SEQ ID NO:22) which had the DNA sequence containing the complete N-terminal amino acid sequence present in the original protein (SEQ ID NO:11). The amino acid sequence (SEQ ID NO:23) encoded by DEHY130 (SEQ ID NO:22) was lacking a start methionine, but comparison with database sequences showing similarity to this protein indicated that, at the most, apparently only 2 to 3 amino acid residues may be lacking, if at all, in addition to a start methionine. Based on this information, a new 5' primer, designated DEHY130NTERM (SEQ ID NO:24), was synthesized to include a start methionine at the beginning of the sequence. Also, the 5' primer (SEQ ID NO:24) and a 3' primer, designated DEHY130CTERM (SEQ ID NO:25), were designed to incorporate Nde I restriction enzyme sites at both ends of the clone for future insertion into the SBET expression vector (14) for production of the protein in *E. coli*. These new primers (SEQ ID NO:24 and SEQ ID NO:25) were used for PCR with 2 ng of plasmid DNA of the previously obtained DEHY130 clone (SEQ ID NO:22) as template. The resulting PCR product of approximately 859 bp (SEQ ID NO:1), designated DEHY133, was cloned directly into a TA vector (Invitrogen). The DNA sequence indicated that the DEHY133 dehydrogenase clone now contained a Met start codon.

In addition, the Nde I fragment from the engineered DEHY133 clone (SEQ ID NO:1) in the TA vector was used as a probe to re-screen 300,000 pfu from the original *F. intermedia* cDNA library. This resulted in numerous strong signals, of which 11 were isolated and screened further. All of the isolated clones provided sequences either similar to, or identical to, the original DEHY133 clone (SEQ ID NO:1). A few of these had additional residues at the N-terminal and contained a start Met, which confirmed that only a few of the N-terminal residues were lacking from the original DEHY130 clone (SEQ ID NO:22). The nucleic acid sequences of four of these clones are set forth in: SEQ ID NO:3 (designated SMDEHY321), SEQ ID NO:5 (designated SMDEHY431), SEQ ID NO:7 (designated SMDEHY511), SEQ ID NO:9 (designated SMDEHY631). Some of these clones, such as SMDEHY133 (SEQ ID NO:1) and SMDEHY631 (SEQ ID NO:9) produced proteins that catalyzed the stereochemical conversion of (−)-secoisolariciresinol into (−)-matairesinol, as set forth below.

Expression in *E. coli* of (−)-Secoisolarciresinol Dehydrogenase.

Since the engineered DEHY133 (SEQ ID NO:1) construct was also in correct reading frame with the lacZ in the original TA cloning vector (Invitrogen), an initial screening for dehydrogenase activity was conducted using the product from an *E. coli* culture harboring this plasmid. The dehydrogenase coding region was also excised using the Nde I sites at the 5' and 3' ends and cloned into the SBET vector. This construct was then transformed into B834(DE3), an *E. coli* strain for overexpression of the cloned dehydrogenase protein.

The *E. coli* culture containing the dehydrogenase clone was grown at 37° C. in 25 ml of SOC Kn50 medium to an O.D. of 0.5. To this was added IPTG to give a final concentration of 0.5 mM and the culture was grown at 18° C. for an additional 20 h. The cells were pelleted at 600×g 4° C. 12 min, resuspended in 5 ml of 20 mM Tris-HCl pH 8.0, 5 mM DTT buffer and repelleted. The final bacterial pellet was resuspended in 200 μL of the above buffer and sonicated 4×15 sec using a Braun-Sonic 2000 sonicator set at maximal output of −0.64. The sample was then centrifuged 20,800 ×g 4° C. 15 min and the crude supernate was assayed for dehydrogenase activity. This protein catalyzed the conversion of labelled (−)-secoisolariciresinol substrate into an intermediary (−)-lactol and further conversion to (−)-matairesinol (see FIGS. 1 and 2). The (+)-antipode of secoisolariciresinol did not serve as a substrate. The clone SMDEHY631 (SEQ ID NO:9) was also expressed in *E. coli* in the foregoing manner.

EXAMPLE 3

Hybridization of Secoisolariciresinol Dehydrogenase cDNA SMDEHY631 (SEQ ID NO:9) to Messenger RNA Molecules Encoding Secoisolariciresinol Dehydrogenase The following procedure was utilized to detect mRNA molecules that encode secoisolariciresinol dehydrogenase in other plant species. Total RNA was isolated from the following plant species: *Forsythia intermedia*(control); *Podophyllum peltatum* (a species that synthesizes the lignan podophyllotoxin); *Linum flavum* (a species that synthesizes the lignan podophyllotoxin) and *Thuja plicata* (a species that synthesizes the lignan plicatic acid). Total RNA was isolated from young leaf tissue by the lithium chloride precipitation method (Dong, J.-Z. & Dunstan, D. I. Plant Cell Reports 15:516–521(1996)). Radiolabelled probe (SMDEHY631 (SEQ ID NO:9)) was prepared using the Pharmacia T7 Quickprime Kit #27-9252-01. The EcoRI/XhoI fragment containing secoisolariciresinol dehydrogenase clone was separated in low melting point (LMP) agarose (GIBCO/BRL Ultrapure LMP Agarose), with the agarose liquefied using AgarAce enzyme (Promega). The isolated probe DNA was boiled for 10 minutes then cooled quickly and briefly on ice and held at 37° C. for 10 minutes. The reaction buffer mixture, enzyme and radioisotope α-$^{32}$P-dCTP were added and the fragment was incubated for 20 minutes at 37° C. The labeled DNA fragment was then separated from unincorporated free radionucleotides by passing through a Centri-Spin 20 column (Princeton Separation).

Total RNA from the foregoing plant species was separated on a 1.3% agarose/formaldehyde gel and blotted onto Amersham Hybond nylon membrane in 10×SSC for 18 hr. The blotted membrane was prehybridized for 5 hr at 42° C. in a prehybridization solution having the following composition: 5×SSPE; 150 μg/ml sheared salmon sperm DNA; 2×Denhardt's solution; 1% SDS; 0.05×BLOTTO and 50% formamide. 0.2 ml prehybridization solution were used per square centimeter of membrane. A 50×stock solution of Denhart's solution contains 5 g Ficoll (Type 400, Pharmacia), 5 g of polyvinylpyrrolidone, 5 g of bovine serum albumin (Fraction V, Sigma) and water to 500 ml. Hybridization was conducted for 16 hr at 42° C. in the same solution that was used for prehybridization. After hybridization was complete, the blot was washed in the following manner: three times in 2×SSPE 30° C. for 5 min per wash; then once in 2×SSPE/0.5% SDS at 30° C. for 10 min. A single hybridizing mRNA band of approximately 1 Kb was visible in each of the blotted RNA samples.

EXAMPLE 4

Hybridization Under Stringent Hybridization Conditions

In one aspect, the present invention provides isolated nucleic acid molecules that hybridize under stringent hybridization conditions to a fragment (having a length of at least 15 bases) of any one of the nucleic acid molecules set forth in SEQ ID NO:1, SEQ ID NO:3, SEQ ID NO:5, SEQ ID NO:7 and SEQ ID NO:9. Hybridization under stringent hybridization conditions is achieved as follows. For high stringency hybridization, nitrocellulose membranes (or other membranes suitable for blotting nucleic acid molecules) are hybridized in 6×SSC, 5×Denhardt's, 0.5% SDS at 55° C. for at least one hour. The hybridized filters are then washed in 2×SSC, 0.5% SDS at 55° C. for at least fifteen minutes. For moderate stringency hybridization, nitrocellulose membranes (or other membranes suitable for blotting nucleic acid molecules) are hybridized in 6×SSC, 5×Denhardt's, 0.5% SDS at 42° C. for at least one hour. The hybridized filters are then washed in 4×SSC (or 6×SSC), 0.5% SDS at 30° C. to 35° C. for at least fifteen minutes. High stringency hybridization conditions are preferably used for hybridization to a nucleic acid molecule from a *Forsythia* species. Moderate stringency hybridization conditions are preferably used for hybridization to a nucleic acid molecule from a species not included in the genus *Forsythia*.

Presently preferred nucleic acid molecules useful for hybridizing to isolated nucleic acid molecules of the present invention include the nucleic acid molecules having the sequences set forth in SEQ ID NO:1, SEQ ID NO:3, SEQ ID NO:5, SEQ ID NO:7 and SEQ ID NO:9. Hybridization in accordance with the present example can be achieved by any art-recognized hybridization procedure such as, for example, by utilizing the technique of hybridizing radiolabelled nucleic acid probes to nucleic acids immobilized on nitrocellulose filters or nylon membranes as set forth, for example, at pages 9.52 to 9.55 of *Molecular Cloning, A Laboratory Manual* (2nd edition), J. Sambrook, E. F. Fritsch and T. Maniatis eds., the cited pages of which are incorporated herein by reference.

The foregoing stringent hybridization conditions can be used to identify nucleic acid molecules encoding secoisolariciresinol dehydrogenase protein from a wide range of plant genuses including, but not limited to Podocarpus, Tsuga, Pinus, Thuja, Araucaria, Juniperus, Taiwania, Virola, Piper, Arctium, Podophyllum and Linum.

While the preferred embodiment of the invention has been illustrated and described, it will be appreciated that various changes can be made therein without departing from the spirit and scope of the invention.

What is claimed is:

1. An isolated nucleic acid molecule encoding a secoisolariciresinol dehydrogenase protein, wherein the isolated nucleic acid molecule hybridizes to the complement of a nucleic acid molecule consisting of the nucleic acid sequence set forth in SEQ ID NO:1 under conditions of 2×SSC at 55° C. for 15 minutes.

2. A nucleic add molecule of claim 1 encoding a secoisolariciresinol dehydrogenase protein consisting of the amino acid sequence of SEQ ID NO:2.

3. A nucleic acid molecule of claim 1 consisting of the nucleic acid sequence of SEQ ID NO:1.

4. A replicable expression vector comprising a nucleic acid sequence encoding a secoisolarciresinol dehydrogenase, wherein the nucleic acid sequence hybridizes to the complement of SEQ ID NO:1 under conditions of 2×SSC at 55° C. for 15 minutes.

5. A replicable expression vector of claim 4 comprising a nucleic acid sequence encoding a secoisolariciresinol dehydrogenase consisting of the amino acid sequence of SEQ ID NO:2.

6. A host cell comprising a replicable expression vector comprising a nucleic acid sequence encoding a secoisolariciresinol dehydrogenase, wherein the nucleic acid sequence hybridizes to the complement of SEQ ID NO:1 under conditions of 2×SSC at 55° C. for 15 minutes.

* * * * *

UNITED STATES PATENT AND TRADEMARK OFFICE
CERTIFICATE OF CORRECTION

PATENT NO. : 6,911,330 B1
DATED : June 28, 2005
INVENTOR(S) : Z.-Q. Xia et al.

It is certified that error appears in the above-identified patent and that said Letters Patent is hereby corrected as shown below:

Title page, Item [54] and Column 1, line 1,
Title, "SECOISOLARICICIRESINOL DEHYDROGENSASE" should read
-- SECOISOLARICIRESINOL DEHYDROGENASE --.

Title page,
Item [56], References Cited, OTHER PUBLICATIONS,
"Herbers" reference, "Paathways" should read -- Pathways --.
Delete the following references:
"Davin, L.B. et al., "Lignin and Lignan Biochemical Paathways in Plants: Unprecedented Discovery in Phenolic Coupling,"*Anais da Academia Brasileira de Ciencias*, 67(3):363-378 (1995).
Umezawa et al., "Formation of Lignans (–)–Secoisolariciresinol and (–)–Matairesinol with Forsythia intermedia Cell-free Extracts," *J. Biol. Chem.*, 266(16):10210-10217 (1991).
Umezawa et al., *J. Chem. Soc. Chem. Commun.*, 1990, 1405-1408.
Umezawa et al., *Biochem. Biophys. Res. Commun.*, 17(3):1008-1014 (1990).".

Item [57], ABSTRACT,
Line 1, "secoisolanciresinol" should read -- secoisolariciresinol --.

Column 1,
Line 59, "*japonicus*and" should read -- *japonicus* and --.

Column 3,
Line 7, "6:143-151(1999))." should read -- 6:143-151 (1999)). --.
Line 35,"Steinbiβ," should read -- Steinbiß, --.

Column 4,
Line 4, "45c:1215-1221(1990))." should read -- 45c:1215-1221 (1990)). --.
Line 8, "(Adlercruetz," should read -- -(Adlercreutz, --.
Line 43, following "*intermedia*" delete "-" [hyphen].

Figures 2A, 2B:
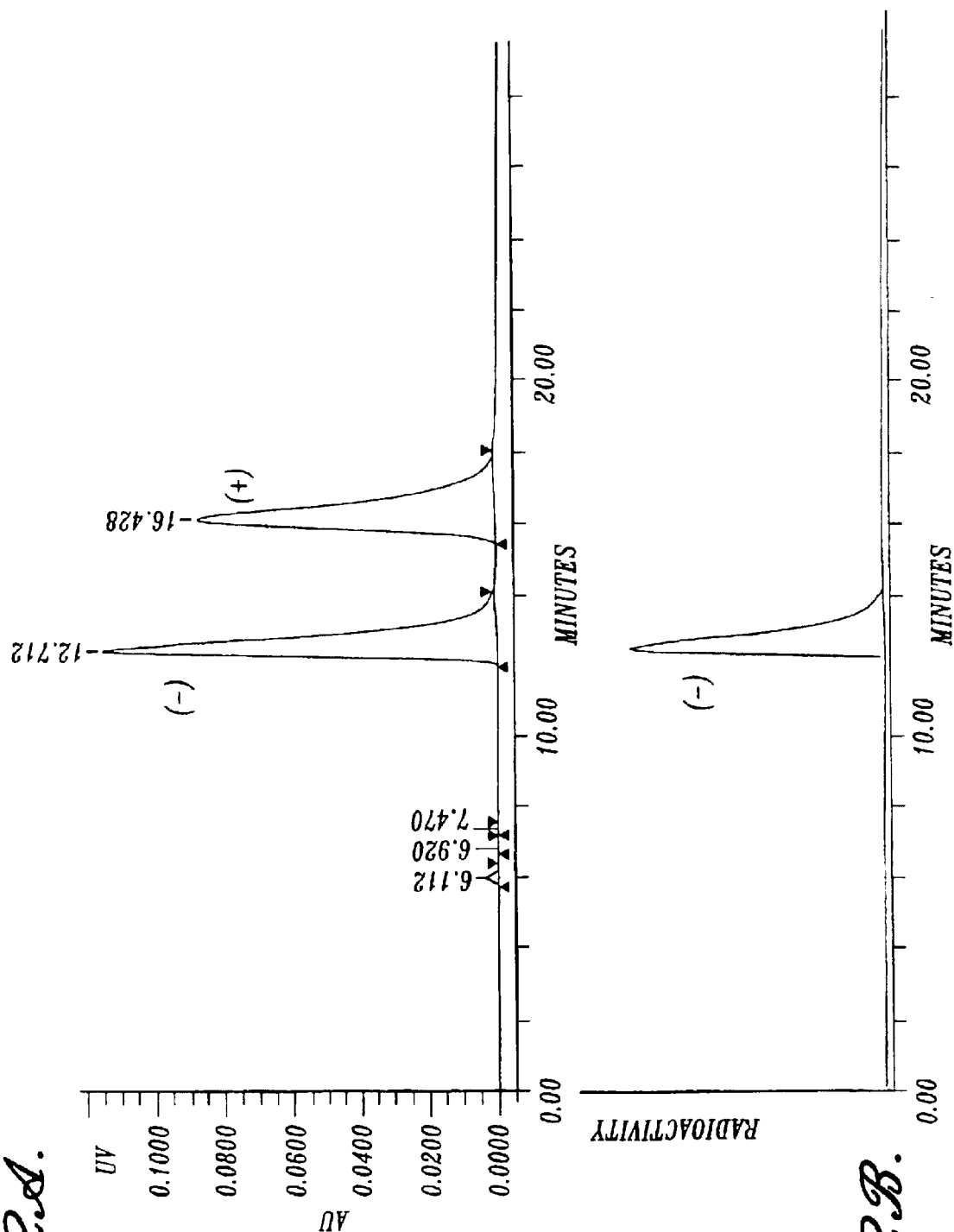
FIG. 2(A) shows chiral HPLC separation of a standard laboratory mixture of (−)-secoisolariciresinol and (+)-secoisolariciresinol.

Column 5,
Line 37, "FIG. (B)" should read -- FIG. 2(B) --.

Column 6,
Line 9, "A,G,C" should read -- A, G, C --.

UNITED STATES PATENT AND TRADEMARK OFFICE
CERTIFICATE OF CORRECTION

PATENT NO. : 6,911,330 B1
DATED : June 28, 2005
INVENTOR(S) : Z.-Q. Xia et al.

It is certified that error appears in the above-identified patent and that said Letters Patent is hereby corrected as shown below:

Column 8,
Line 19, "DEHY30RevB" should read -- DEHYF30RevB --.
Line 32, "DEHYF30REVB" should read -- DEHYF30RevB --.
Line 36, "cloned into TA vector," should read -- cloned into a TA vector, --.
Line 51, "5(primer," should read -- 5' primer, --.

Column 9,
Line 30, "biologicalproperties," should read -- biological properties, --.

Column 11,
Line 26, "beteroduplex" should read -- heteroduplex --.

Column 12,
Line 1, "Boculovirus" should read -- Baculovirus --.
Line 23, "promoter/secoisoiariciresinol" should read -- promoter/secoisolariciresinol --.
Line 58, "(Jones,*Genetics*" should read -- (Jones, *Genetics* --.

Column 13,
Line 42, "*Bio l.*" should read -- *Biol.* --.
Lines 48-49, "*Trasgenic*" should read -- *Transgenic* --.
Line 57, "secoisolarciresinol" should read -- secoisolariciresinol --.

Column 14,
Lines 39-40, "10(7):239-246" should not break.
Line 59, "brocolli," should read -- broccoli, --.
Line 61, "raddichio);" should read -- radicchio); --.

Column 15,
Line 3, "Chenopodacum" should read -- Chenopodiacum --.
Line 21, "Aclinidia" should read -- Actinidia --.
Line 65, "insure" should read -- ensure --.

Column 16,
Line 7, "(Urlab" should read -- (Urlaub --.
Line 35, "BgII" should read -- BglI --.

Column 17,
Line 40, "(His$_6$).Tag" should read -- (His)$_6$·Tag --.

UNITED STATES PATENT AND TRADEMARK OFFICE
CERTIFICATE OF CORRECTION

PATENT NO. : 6,911,330 B1
DATED : June 28, 2005
INVENTOR(S) : Z.-Q. Xia et al.

It is certified that error appears in the above-identified patent and that said Letters Patent is hereby corrected as shown below:

Column 18,
Line 1, "pUCI18," should read -- pUC1 18, --.
Line 8, "(penicilinase)" should read -- (penicillinase) --.
Line 34, "proalburin" should read –proalbumin --.
Line 43, "al.,Gene" should read -- al., Gene --.

Column 20,
Line 15, "2',5' -diphosphate-Sepharose" should read -- 2',5'-diphosphate-Sepharose --.
Line 46, "(Thernolyne)" should read -- (Thermolyne) --.

Column 21,
Line 6, "266: 10210-10217(1991)." should read -- 266:10210-10217 (1991). --.
Line 10, "Secoisolarciresinol" should read -- Secoisolariciresinol --.
Line 15, "$\mu$1 )." should read -- $\mu$1). --.
Line 37, "EtoAc" should read -- EtOAc --.

Column 22,
Line 6, "307(1981))." should read -- 307 (1981)). --.

Column 23,
Line 38, "15:516-521(1996))" should read -- 15:516-521 (1996)) --.
Line 39, "*plants*" should not be italicized.
Line 41, "(Oligotex-dt(Suspension," should read -- (Oligotex-dt Suspension, --.
Line 42, "ZAP-cDNAII" should read -- ZAP-cDNA II --.
Line 46, "*Edition*" should not be italicized.

Column 24,
Line 4, "DEHY30RevB" should read -- DEHYF30RevB --.
Line 47, "198:78(1996))." should read -- 198:78 (1996)). --.
Line 65, "DEHYF30REVB" should read -- DEHYF30RevB --.

Column 25,
Line 54, "(-)-Secoisolarciresinol" should read -- (-)-Secoisolariciresinol --.

Column 26,
Line 24, "*intermedia*(control);" should read -- *intermedia* (control); --.
Line 31, "15:516-521(1996))." should read -- 15:516-521 (1996)). --.
Line 53, "Denhart's" should read -- Denhardt's --.

UNITED STATES PATENT AND TRADEMARK OFFICE
CERTIFICATE OF CORRECTION

PATENT NO. : 6,911,330 B1
DATED : June 28, 2005
INVENTOR(S) : Z.-Q. Xia et al.

It is certified that error appears in the above-identified patent and that said Letters Patent is hereby corrected as shown below:

Column 55,
Line 29, "nucleic add" should read -- nucleic acid --.
Line 35, "secoisolarciresinol" should read -- -secoisolariciresinol --.

Signed and Sealed this

Twentieth Day of December, 2005

JON W. DUDAS
*Director of the United States Patent and Trademark Office*